United States Patent
Yarbro et al.

(10) Patent No.: US 9,310,338 B2
(45) Date of Patent: Apr. 12, 2016

(54) METHOD FOR MEASURING REMOTE FIELD EDDY CURRENT THICKNESS IN MULTIPLE TUBULAR CONFIGURATION

(75) Inventors: Gregory Scott Yarbro, Casper, WY (US); Jing Li, Pearland, TX (US); Michael Bittar, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 225 days.

(21) Appl. No.: 13/878,553

(22) PCT Filed: Oct. 11, 2011

(86) PCT No.: PCT/US2011/055675
§ 371 (c)(1),
(2), (4) Date: Apr. 9, 2013

(87) PCT Pub. No.: WO2012/051136
PCT Pub. Date: Apr. 19, 2012

(65) Prior Publication Data
US 2013/0193953 A1    Aug. 1, 2013

Related U.S. Application Data

(60) Provisional application No. 61/393,282, filed on Oct. 14, 2010.

(51) Int. Cl.
*G01N 27/90*        (2006.01)
*E21B 47/08*        (2012.01)
*G01B 7/06*         (2006.01)
*G01N 33/20*        (2006.01)
*G01V 3/12*         (2006.01)

(52) U.S. Cl.
CPC .......... *G01N 27/9066* (2013.01); *E21B 47/082* (2013.01); *G01B 7/10* (2013.01); *G01N 33/20* (2013.01); *G01V 3/12* (2013.01)

(58) Field of Classification Search
CPC ....... G01N 22/00; G01N 29/11; G01N 29/22; G01N 27/82; G01N 27/9033; G01N 27/9093; E21B 47/082; G01R 33/04; G01B 7/10; G01B 7/312; G01V 3/28
See application file for complete search history.

(56) References Cited

U.S. PATENT DOCUMENTS 2,573,799 A  *  11/1951  MacLean ................. G01B 7/10
                                                    324/119
2,858,108 A  *  10/1958  Wise ......................... E21B 7/24
                                                    175/103
(Continued)

OTHER PUBLICATIONS

Remote Field Eddy Current Inspection by David L Atherton, IEEE Transactions on Magnetics, vol. 31, No. 6, Nov. 1995, pp. 4142-4147, PDF document attached.*
(Continued)

*Primary Examiner* — Jermele M Hollington
*Assistant Examiner* — Suresh K Rajaputra
(74) *Attorney, Agent, or Firm* — Haynes and Boone, LLP

(57) ABSTRACT

In accordance with aspects of the present invention, a method of inspecting a well tubular is disclosed. The method utilizes a probe with a transmitter and detectors spaced from the transmitter by at least twice the diameter of the pipe to be tested. In some cases where multi-tubular structures are tested, the probe can include further detectors spaced from the transmitter by at least twice the diameter of the outer pipes as well. The phase of signals detected by the detectors relative to the transmitter are utilized to detect faults in the pipes.

13 Claims, 19 Drawing Sheets

(56) References Cited

U.S. PATENT DOCUMENTS

| | | | | |
|---|---|---|---|---|
| 3,060,377 A * | 10/1962 | Schmidt | E21B 47/082 | 324/220 |
| 3,091,733 A * | 5/1963 | Fearon | G01N 27/902 | 324/220 |
| 3,100,281 A * | 8/1963 | Spanner | G01B 7/312 | 324/233 |
| 3,234,457 A * | 2/1966 | Sower | G01N 27/9033 | 324/241 |
| 3,461,218 A * | 8/1969 | Buchhold | H01B 12/12 | 174/13 |
| 3,532,969 A * | 10/1970 | McCullough | G01B 7/10 | 324/229 |
| 3,609,531 A * | 9/1971 | Forster | G01N 27/904 | 324/227 |
| 3,906,358 A * | 9/1975 | Stone | F22B 37/003 | 324/220 |
| 3,916,301 A * | 10/1975 | Vild | G01N 27/9046 | 324/226 |
| 3,940,689 A * | 2/1976 | Johnson, Jr. | E21B 47/082 | 324/221 |
| 4,107,605 A * | 8/1978 | Hudgell | G01N 27/9033 | 324/220 |
| 4,285,242 A * | 8/1981 | Braithwaite | G01N 29/265 | 324/220 |
| 4,292,589 A * | 9/1981 | Bonner | E21B 47/082 | 324/221 |
| 4,325,026 A * | 4/1982 | Cooper, Jr. | G01B 7/14 | 324/219 |
| 4,510,447 A * | 4/1985 | Moyer | G01N 27/902 | 324/225 |
| 4,576,097 A * | 3/1986 | Foster | B08B 9/0551 | 104/138.2 |
| 4,578,643 A * | 3/1986 | Junker | G01N 27/9086 | 324/202 |
| 4,598,250 A * | 7/1986 | Lorenzi | G01N 27/82 | 324/220 |
| 4,602,212 A * | 7/1986 | Hiroshima | G01N 27/9046 | 324/227 |
| 4,631,688 A * | 12/1986 | Boehm | G01N 27/9046 | 324/216 |
| 4,677,379 A * | 6/1987 | Arnaud | G01N 27/9046 | 324/240 |
| 4,686,471 A * | 8/1987 | Morita | B21B 38/02 | 324/225 |
| 4,700,134 A * | 10/1987 | Scharton | G01N 27/72 | 324/202 |
| 4,708,204 A * | 11/1987 | Stroud | E21B 47/09 | 166/255.1 |
| 4,789,827 A * | 12/1988 | Bergander | G01N 27/82 | 324/220 |
| 4,839,593 A * | 6/1989 | Spies | G01N 17/00 | 324/240 |
| 4,843,319 A * | 6/1989 | Lara | G01N 27/9053 | 324/229 |
| 4,843,320 A * | 6/1989 | Spies | G01N 17/00 | 324/229 |
| 4,862,079 A * | 8/1989 | Chickering | G21C 17/06 | 324/226 |
| 4,945,306 A * | 7/1990 | Lowther | G01N 27/82 | 324/220 |
| 5,038,107 A * | 8/1991 | Gianzero | G01V 3/28 | 324/339 |
| 5,210,492 A * | 5/1993 | Hosohara | G01N 27/9046 | 324/220 |
| 5,233,297 A * | 8/1993 | Lara | E21B 47/082 | 324/220 |
| 5,237,270 A * | 8/1993 | Cecco | G01N 27/904 | 324/220 |
| 5,283,520 A * | 2/1994 | Martin | G01V 3/28 | 324/220 |
| 5,454,276 A * | 10/1995 | Wernicke | G01N 27/9013 | 324/220 |
| 5,537,035 A * | 7/1996 | Fowler | G01N 27/82 | 324/220 |
| 5,565,633 A * | 10/1996 | Wernicke | G01N 27/9013 | 324/220 |
| 5,617,024 A * | 4/1997 | Simpson | G01N 27/902 | 324/209 |
| 5,623,204 A * | 4/1997 | Wilkerson | G01N 27/9033 | 324/220 |
| 5,675,251 A * | 10/1997 | MacLean | G01N 27/902 | 324/220 |
| 5,739,685 A * | 4/1998 | Suzuma | G01N 27/82 | 324/225 |
| 5,821,747 A * | 10/1998 | Atherton | G01N 27/902 | 165/11.2 |
| 5,828,213 A * | 10/1998 | Hickman | G01N 27/82 | 324/232 |
| 5,864,229 A * | 1/1999 | Lund | G01N 27/902 | 324/240 |
| 5,864,232 A * | 1/1999 | Laursen | G01N 27/902 | 324/220 |
| 5,881,310 A * | 3/1999 | Airhart | E21B 47/124 | 710/3 |
| 5,942,893 A * | 8/1999 | Terpay | G01N 27/9033 | 324/164 |
| 5,942,894 A * | 8/1999 | Wincheski | G01N 27/902 | 324/220 |
| 5,963,042 A * | 10/1999 | Suyama | G01N 22/02 | 324/326 |
| 6,005,396 A * | 12/1999 | Suyama | G01N 22/02 | 324/528 |
| 6,013,158 A * | 1/2000 | Wootten | B01D 53/24 | 202/100 |
| 6,018,242 A * | 1/2000 | Piriou | G01N 27/9033 | 324/241 |
| 6,023,986 A * | 2/2000 | Smith | G01C 7/06 | 324/220 |
| 6,087,830 A * | 7/2000 | Brandly | G01M 3/005 | 324/220 |
| 6,127,823 A * | 10/2000 | Atherton | G01N 27/902 | 324/220 |
| 6,154,167 A * | 11/2000 | Annan | G01S 13/0209 | 342/175 |
| 6,194,902 B1 * | 2/2001 | Kuo | G01N 17/00 | 324/535 |
| 6,265,870 B1 * | 7/2001 | Weischedel | G01N 27/902 | 324/220 |
| 6,291,992 B1 * | 9/2001 | van Andel | G01N 27/904 | 324/230 |
| 6,339,327 B1 * | 1/2002 | Potiquet | G01N 27/902 | 324/220 |
| 6,359,434 B1 * | 3/2002 | Winslow | G01N 27/9046 | 324/220 |
| 6,429,650 B1 * | 8/2002 | Kwun | G01N 29/11 | 324/220 |
| 6,504,363 B1 * | 1/2003 | Dogaru | G01N 27/9006 | 324/235 |
| 6,583,618 B2 * | 6/2003 | McClelland | G01N 27/72 | 324/239 |
| 6,636,037 B1 * | 10/2003 | Ou-Yang | G01N 27/902 | 324/232 |
| 6,683,452 B2 * | 1/2004 | Lee | G01N 27/82 | 324/220 |
| 6,683,641 B1 * | 1/2004 | MacCracken | F01D 5/005 | 348/82 |
| 6,703,831 B1 * | 3/2004 | Keely | G01N 27/904 | 324/232 |
| 6,751,560 B1 * | 6/2004 | Tingley | G01N 22/02 | 702/51 |
| 6,781,369 B2 * | 8/2004 | Paulson | G01N 27/82 | 324/220 |
| 6,967,478 B2 * | 11/2005 | Wayman | G01N 27/82 | 324/235 |
| 7,002,340 B2 * | 2/2006 | Atherton | G01N 33/383 | 321/220 |
| 7,143,659 B2 * | 12/2006 | Stout | F17D 5/00 | 324/71.2 |
| 7,218,102 B2 * | 5/2007 | Nestleroth | G01N 27/82 | 324/220 |
| 7,301,335 B2 * | 11/2007 | Sun | G01N 27/82 | 324/232 |

(56) References Cited

U.S. PATENT DOCUMENTS

| | | | | |
|---|---|---|---|---|
| 7,336,078 B1* | 2/2008 | Merewether | ............ | G01V 3/15 324/326 |
| 7,403,000 B2* | 7/2008 | Barolak | ............... | E21B 47/082 324/221 |
| 7,443,154 B1* | 10/2008 | Merewether | ........... | G01V 3/104 324/326 |
| 7,528,599 B2* | 5/2009 | Zimmerman | ...... | G01N 27/9033 324/220 |
| 7,560,920 B1* | 7/2009 | Ouyang | ............... | G01N 27/902 324/240 |
| 7,626,383 B1* | 12/2009 | Sun | ........................ | G01N 27/82 324/232 |
| 7,705,589 B2* | 4/2010 | Kim | ................... | G01N 27/9033 324/228 |
| 7,719,266 B1* | 5/2010 | Zamanzadeh | ...... | G01R 33/1223 324/228 |
| 7,755,360 B1* | 7/2010 | Martin | ..................... | G01V 3/15 324/326 |
| 7,772,839 B2* | 8/2010 | Watson | .............. | B60R 21/0136 324/228 |
| 7,821,247 B2* | 10/2010 | Fagbayi | ................ | C23F 13/043 324/71.1 |
| 8,079,414 B2* | 12/2011 | Smaardyk | ............... | E21B 47/09 166/250.13 |
| 8,159,217 B2* | 4/2012 | Decitre | ............. | G01N 27/9046 324/241 |
| 8,264,226 B1* | 9/2012 | Olsson | ................... | G01V 3/15 324/326 |
| 8,274,279 B2* | 9/2012 | Gies | .................. | G01N 27/9033 324/200 |
| 8,283,918 B2* | 10/2012 | Park | ...................... | B24B 49/105 324/220 |
| 8,373,411 B2* | 2/2013 | Couchman | ............. | F16L 55/28 324/220 |
| 8,378,667 B2* | 2/2013 | Miska | ..................... | F16L 55/48 324/207.22 |
| 8,427,179 B2* | 4/2013 | Chamberlin | ........ | F16L 37/0985 324/682 |
| 8,536,860 B2* | 9/2013 | Boenisch | ............. | G01N 27/90 324/220 |
| 8,552,718 B2* | 10/2013 | Groos | .................... | G01N 27/87 324/237 |
| 2001/0017541 A1 | 8/2001 | Kwun | .................... | G01N 22/00 324/240 |
| 2003/0089267 A1* | 5/2003 | Ghorbel | .................. | F16L 55/38 104/138.1 |
| 2003/0164698 A1* | 9/2003 | Paulson | ................. | G01N 27/82 324/220 |
| 2004/0041560 A1* | 3/2004 | Walters | .................. | G01N 27/82 324/238 |
| 2004/0050167 A1* | 3/2004 | Linares | ................ | G01N 29/225 73/622 |
| 2004/0095137 A1* | 5/2004 | Kwun | .................. | G01N 29/2412 324/240 |
| 2004/0130322 A1* | 7/2004 | Crouzen | .................. | G01B 7/10 324/229 |
| 2004/0134970 A1* | 7/2004 | Den Boer | ............... | B23K 31/12 228/104 |
| 2004/0173116 A1* | 9/2004 | Ghorbel | ................. | F16L 55/26 104/138.2 |
| 2005/0237055 A1 | 10/2005 | Sun et al. | | |
| 2006/0006875 A1* | 1/2006 | Olsson | ................... | G01V 3/081 324/338 |
| 2006/0087448 A1* | 4/2006 | Den Boer | .............. | E21B 17/006 340/854.2 |
| 2006/0247868 A1* | 11/2006 | Brandstrom | .......... | G01N 27/82 702/35 |
| 2007/0042716 A1* | 2/2007 | Goodall | ................ | H04W 16/18 455/67.11 |
| 2007/0151344 A1* | 7/2007 | Meethal | ............. | G01N 29/2412 73/649 |
| 2007/0205764 A1* | 9/2007 | Kroner | ............... | G01N 27/9033 324/228 |
| 2007/0222436 A1* | 9/2007 | Gao | ........................ | G01N 27/82 324/220 |
| 2009/0160437 A1* | 6/2009 | Kroner | ............... | G01N 27/9033 324/240 |
| 2009/0166035 A1* | 7/2009 | Almaguer | ............... | E21B 7/061 166/254.1 |
| 2009/0242200 A1* | 10/2009 | Badoux | .............. | G01N 27/9033 166/255.2 |
| 2010/0206064 A1* | 8/2010 | Estes | ....................... | E21B 47/01 73/152.57 |
| 2010/0207711 A1* | 8/2010 | Estes | .................... | E21B 47/082 333/24 C |
| 2011/0127999 A1* | 6/2011 | Lott | ........................ | G01R 33/04 324/239 |
| 2011/0163740 A1* | 7/2011 | Russell | .................. | G01N 27/72 324/220 |
| 2013/0193953 A1* | 8/2013 | Yarbro | .................. | E21B 47/082 324/76.77 |
| 2014/0236499 A1* | 8/2014 | St-Laurent | ......... | G01N 29/0645 702/36 |
| 2014/0311245 A1* | 10/2014 | Horoshenkov | .......... | G01N 29/11 73/592 |

OTHER PUBLICATIONS

Xingfu et al "Multi-Pipe String Electromagnetic Detection Tool and Its Applications" ICEMI' 2007, Proceedings of the The Eighth International Conference on Electronic Measurement and Instruments, pp. 4-423 to 4-427, PDF attached.*

International Search Report of the International Searching Authority issued in Application No. PCT/US2011/055675, date of mailing Feb. 1, 2012, 4 pages.

Written Opinion of the International Searching Authority issued in Application No. PCT/US2011/055675, date of mailing Feb. 1, 2012, 10 pages.

PCT International Preliminary Report on Patentability issued in Application No. PCT/US2011/055675, dated of mailing Oct. 23, 2012, 15 pages.

Patent Examination Report, Australian Patent Application No. 2011313872, Dec. 19, 2013, Australian Government IP Australia.

Patent Examination Report, Canadian Patent Application No. 2,813,745, Sep. 26, 2013, Canadian Intellectual Property Office.

Office Action, Mexican Patent Application No. MX/a/2014/004119, Jul. 29, 2014, Mexican Patent Office.

Examination Report, GCC Patent Application No. GC 2012-20678, Nov. 10, 2015, 3 pages, Patent Office of the Cooperation Council for the Arab States of the Gulf.

* cited by examiner

METHOD FOR MEASURING REMOTE FIELD EDDY CURRENT THICKNESS IN MULTIPLE TUBULAR CONFIGURATION

RELATED APPLICATIONS

The present application claims priority to U.S. Provisional Application 61/393,282, filed on Oct. 14, 2010, by Yarbro et al., entitled "Method for Measuring Remote Field Eddy Current Thickness in Multiple Tubular Configuration," which is herein incorporated by reference in its entirety.

TECHNICAL FIELD

The present invention relates to measurement of thicknesses in tubular configurations utilizing remote field eddy currents and to remote field eddy current measurement in single or multiple tubular with magnetic permeability variations.

DISCUSSION OF RELATED ART

Aging oilfield tubular create environmental and economic risk to operators. Early identification and remediation is key to mitigating these hazards. Remote Field Eddy Current inspection techniques are commonly used to evaluate the thickness of down hole tubular and detect defects. The technique is viable in single tubular configurations. However, in multiple string configuration, the resultant response is typically the sum of the combined thickness.

Further, the method assumes that the relative magnetic permeability ($\mu_r$) and the electrical conductivity ($\delta_{o/o}$) remain constant over the logged interval. In reality, magnetic permeability often changes over short intervals due to previous well intervention activities (wire line, CCL magnets, and coil-tubing operations) and from stress changes in the pipe. These magnetic anomalies create false thickness changes that can be difficult to identify and are often assumed to be pipe defects. False defects reduces confidence in the analysis of the results. Aging oilfield tubular create environmental and economic risk to operators. Early identification and remediation of faulty pipes is key to mitigating hazards.

Therefore, there is a need to develop better methods of determining thicknesses and evaluating pipes.

SUMMARY

In accordance with aspects of the present invention, a method of inspecting a well tubular is disclosed. In some embodiments, a method of inspecting a pipe includes lowering a probe into the pipe, the probe including a transmitter and at least one detector separated from the transmitter by a separation distance equal to or greater than twice the diameter of the pipe; providing a driving signal to the transmitter; receiving detector signals from the one or more detectors; determining the phase shift between the detector signals and the driving signal; and determining faults along the pipe based on the phase shift. In some embodiments, determining a fault in the pipe based on the phase shift includes modeling a response of the probe to the fault. In some embodiments, a partial saturation step may also be performed.

A probe for testing a pipe includes a transmitter; and one or more detectors separated from the transmitter by a distance at least twice that of the inner diameter of the pipe. In some embodiments, one or more second detectors can be included, the second detectors being spaced from the transmitter by a distance at least twice that of the inner diameter of a second pipe that is concentric with the pipe.

A system for testing a pipe can include a controller; and a probe coupled to the controller, the probe included a transmitter and one or more detectors separated from the transmitter by a distance at least twice that of the inner diameter of the pipe. In some embodiments, the controller includes a transmitter driver coupled to the transmitter; a detection circuit coupled to the one or more detectors; and a processor, the processor coupled to the transmitter driver and the detection circuit to determine the phase of signals received at the detectors relative to the signal provided by the transmitter driver.

These and other embodiments are further discussed below with respect to the following figures.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other material that, although not specifically described here, is within the scope and the spirit of this disclosure.

Techniques according to some embodiments of the present invention are capable of separating and quantifying the thickness of each of a multiple tubular arrangement. Some techniques according to embodiments of the present invention can also be utilized to identify permeability induced false responses and allow for a qualitative analysis.

Figure 1A:
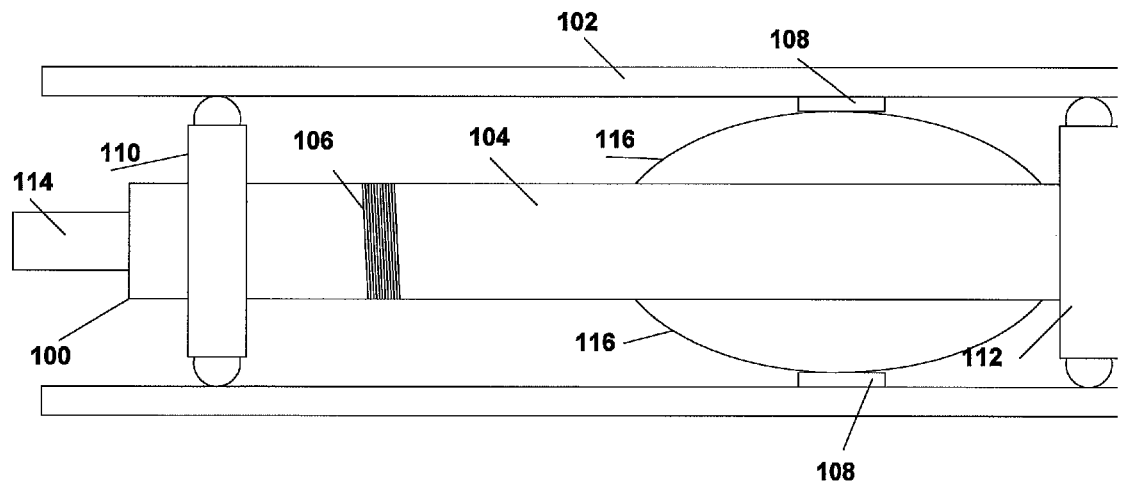
FIG. 1A illustrates a probe according to some embodiments of the present invention.

FIG. 1A illustrates an example of an eddy inner probe 100 according to some embodiments of the present invention. As shown in FIG. 1, a transmitter coil 106 is utilized to transmit electromagnetic waves. Eddy currents are established on the surfaces of the wall of pipe 102. One or more detectors 108, which are separated from transmitter 106, receive the electromagnetic waves transmitted through the wall of pipe 102. Detectors 108 can be configured on either side of transmitter 106, or there may be detectors 108 distributed on both sides of transmitter 106. In the embodiment shown in FIG. 1A, detectors 1A are mounted on spring arms 116 that hold detectors against the wall of pipe 102. There may be any number of detectors 108 distributed at different axial locations against the wall of pipe 102. In some embodiments 12 detectors distributed at 30° angular separations can be utilized.

As shown in FIG. 1A, detector signals and transmission signals can be transported to transmitter 106 and detectors 108 through a cable 114. Probe 100 can be inserted as part of a drill string or can be wire-lined into pipe 106 for the test. A mounting material 104 can be utilized to mount transmitter 106 and detectors 108. In some embodiments, spacers 110 and 112 can be utilized to center probe 100 in pipe 102, although in some embodiments centering probe 100 in pipe 102 can be accomplished by other components surrounding probe 100.

Figure 1B:
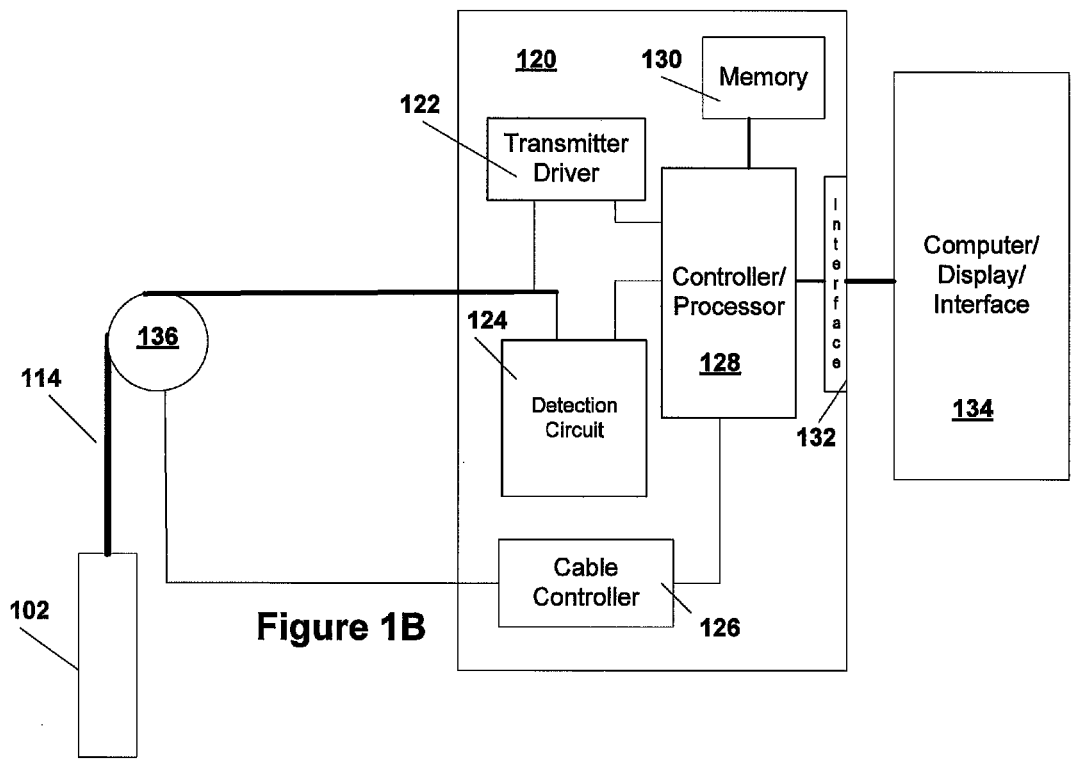
FIG. 1B illustrates a control system for the probe illustrated in FIG. 1A.

As shown in FIG. 1B, cable 114 can be electrically coupled to a controller 120. Cable 114 includes all of the electrical couplings to transmitter 106 and to detectors 108. Further, cable 114 can include mechanical structure for allowing the raising and lowering of probe 100 into pipe 102. Cable 114 can, for example, be formed of a cable with electrical wiring included to allow for wireline testing, or can be part of a drill string. Further, parts of controller 120 can be included within probe 100. For purposes of this description, an example where controller 120 is at the surface while testing of pipe 102 is undertaken is described.

As shown in FIG. 1B, probe 100, attached to cable 114, can be raised and lowered in pipe 102 by a winch 136. At least the electrical wirings of cable 114 are input to controller 120. Controller 120 includes a transmitter driver 122, a detection circuit 124, and a controller 128. Controller 120 can also include a cable controller 126 that controls winch 136 according to signals from controller 128 and, in some embodiments, provides data related to the position of probe 100 along pipe 102 to controller 128. Controller 128 can further be coupled to a memory 130. Memory 130 can include both volatile and non-volatile memory and can store programming and data for controller 128. Controller 128 an also be coupled through an interface 132 to computer 134. Computer 134 may include a display and user interface device (e.g., keyboard, pointing device, etc.), may include fixed storage devices such as hard drives, and may include processors and software for analyzing data captured by controller 128. Controller 128 may be, for example, a processor or other devices for receiving and processing data.

Controller 128 is coupled to control transmitter driver 122 and to receive signals from detection circuit 124. Transmitter driver 122 provides driving signals to transmitter 106. Signals from detectors 108 are received into detection circuit 124 and are provided to controller 128 for processing. Controller 128, then, can compare the signal from transmitter 106 to the signals received at detectors 108.

The remote Field Eddy Current (RFEC) inspection technique is a non-destructive testing method for the evaluation of a pipe wall thickness. As discussed above with respect to FIGS. 1A and 1B, the RFEC inspection technique involves an inner probe 100 that includes a transmitter coil 106 and either a single or multiple sensors 108 at some distance from transmitting coil 106. In some embodiments, a low frequency sinusoidal current (e.g., 5 Hz to 200 Hz) drives transmitting coil 106, producing alternating eddy currents on the interior of pipe 102. These eddy currents travel down the inside of pipe 102 and simultaneously diffuse through the wall of pipe 102 to travel along the outside of pipe 102 as well. The eddy current then produces a signal at detectors 108. The properties of pipe 102 affect the speed of these transmission paths and the attenuation of the received signal.

Figure 2:
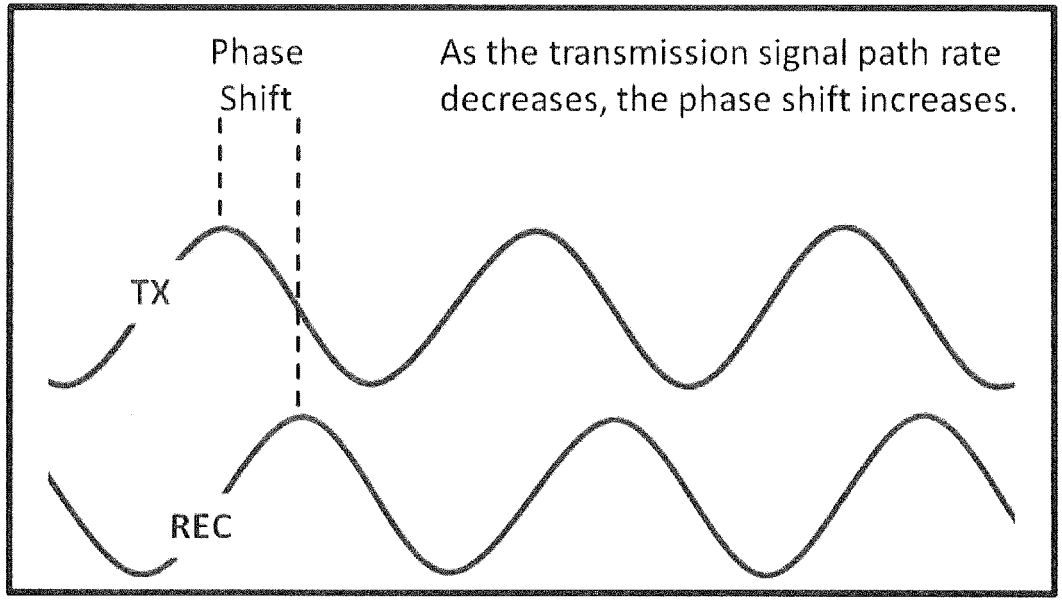
FIG. 2 illustrates a phase shift measurement between a transmitter and receiver in an eddy current measurement.

FIG. 2 illustrates that a phase shift occurs between the signal transmitted from transmitter 106 and the signal received at detectors 108 in a single pipe configuration. The primary measurement in RFEC is the determination of the time it takes for the transmitted signal to travel from transmitter 106 to one or more of the detectors 108. This determination is achieved by measuring the phase difference between the transmitter driver current at transmitter 106 and the received detector signal at one or more of detectors 108. For a given separation between transmitter 106 and detectors 108 and transmitter frequency, an increase in the phase separation indicates a slower transmission path.

Figure 3:
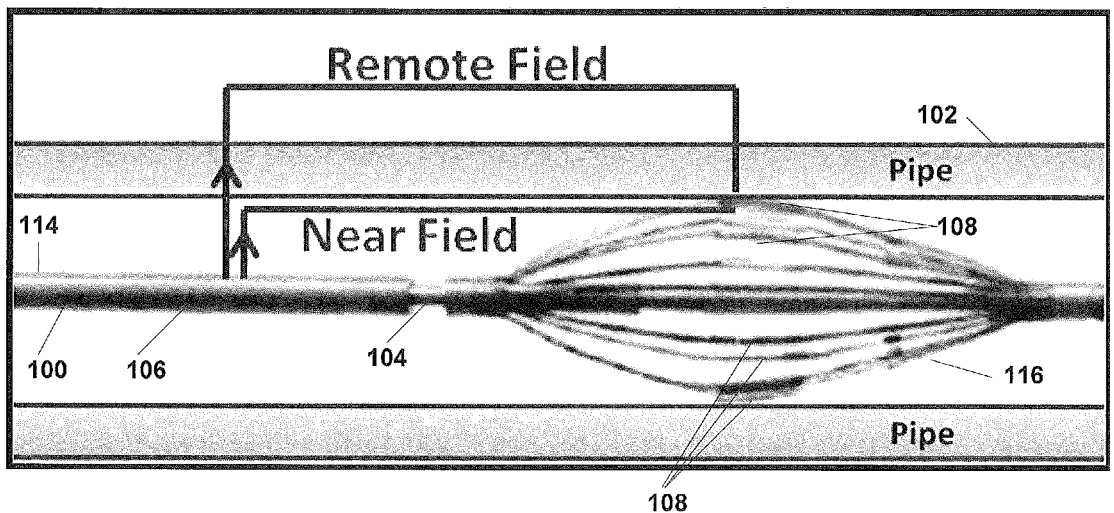
FIG. 3 illustrates the detector system and near field and remote field measurements according to some embodiments of the present invention.

FIG. 3 illustrates an RFEC probe 100 according to some embodiments of the present invention as well as the near field and remote field transmission paths. In the embodiment of probe 100 illustrated in FIG. 2, detectors 108 are held against the wall of pipe 102 by spring arms 116. Spring arms 116 help to minimize stand-off effects and can provide an indication of small defects on one side of pipe 102. Centering devices 110 and 112, which are not shown in FIG. 3, can be mounted above and below probe 100.

As shown in FIG. 3, the alternating electromagnetic field radiating from transmitter 106 creates alternating eddy currents on the inner surface of pipe 102. Two separate paths exist for the transmission of the signal radiated from transmitter 106. These two paths are referred to as the Near Field and the Remote Field. The Near Field signal travels down the inner wall of pipe 102, while the Remote Field signal travels through the wall of pipe 102 near transmitter 106 along the outside of pipe 102, and then back through the wall of pipe 102 near detectors 108. As will be discussed latter, it is important to note that the Remote Field passes through the wall of pipe 102 twice.

Figure 4A:
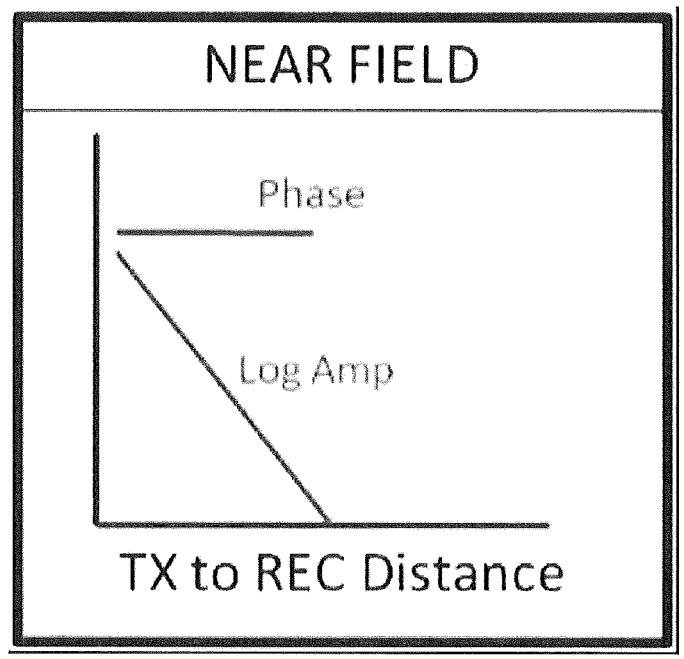
FIG. 4A illustrates the relationship between the phase and amplitude of the near field received signal with increasing transmitter to detector spacing.

For the internal eddy currents (Near Field), pipe 102 behaves as a wave-guide. However, as the frequency utilized in the RFEC inspection is below the cutoff frequency for a wave-guide corresponding to pipe 102 under inspection, these internally transmitted waves are highly attenuated. At a distance of approximately two pipe diameters from transmitting coil 106, this Near Field signal is essentially zero. The transmission speeds of the Near Field signal path is extremely fast, resulting in little phase shift with increasing spacing between transmitter 106 and detectors 108. The relationship between the Phase and Amplitude of the received signal with increasing spacing between transmitter 106 and detectors 108 is shown in FIG. 4A. As is shown in FIG. 4, although the phase stays substantially constant over the distance, the amplitude decreases to zero with increasing distance between transmitter 106 and detectors 108.

Figure 4B:
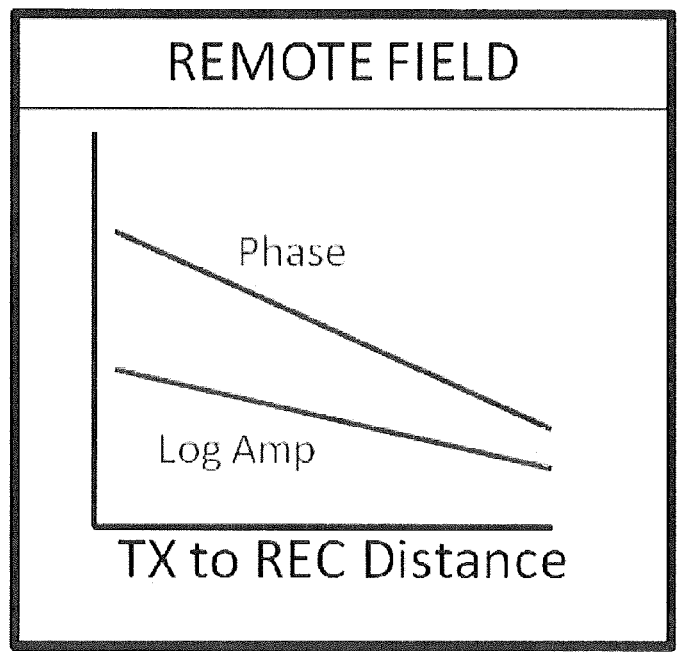
FIG. 4B illustrates the relationship between the phase and amplitude of the remote field received signal with increasing transmitter to detector spacing.

The relationship between the phase and amplitude of the received signal with increasing spacing between transmitter 106 and detectors 108 is shown in FIG. 4B. As is shown in FIG. 3, the eddy currents produced on the interior wall of pipe 102 also diffuses through the wall of pipe 102. This signal then radiates out away from the outer wall of pipe 102 and travels down the outer wall of pipe 102 to re-diffuse through the wall of pipe 102 to be received by detectors 108. The attenuation of the signal along this path, the remote field path, is significantly less than that of the Near Field attenuation. The rate of transmission of the remote field signal as it diffuses through pipe 102 is relatively slow, resulting in increasing phase shift with increasing thickness of pipe 102. As the signal path involves traversing the wall of pipe 102 two times, the resultant phase shift is therefore directly proportional to twice the thickness of pipe 102. Transmission along the outside wall of pipe 102 is relatively fast and consistent, as is the transmission between the inner wall of pipe 102 to detectors 108, resulting in little affect for small amounts of detector lift off. As shown in FIG. 4B, the phase of the remote field distance decreases with increasing distance between transmitter 106 and detectors 108. Additionally, the amplitude decreases with increasing distance between transmitter 106 and detectors 108, but does not decrease as much as does the near field signal with increasing distance between transmitter 106 and detector 108.

Detectors 108 typically only record one of the near field or the remote field signals. Consequently, the signal at detectors 108 with the largest amplitude will dominate the recorded phase shift measurement. As the attenuation of the two paths is significantly different, the desired field may be obtained by altering the spacing between transmitter 106 and detectors 108. As the spacing is increased, the Near Field signal is attenuated to the point that the Remote Field dominates the received signal. The received signal changes from the Near Field signal to the Remote Field signal at approximately two (2) times the diameter of pipe 102. In some embodiments of the invention, for example, the spacing between transmitter 106 and one of detectors 108 is about 18 inches, which is more than twice the diameter of a typical pipe diameter for a 7" pipe. Actual distance between transmitter 106 and detectors 108 is determined by the diameter of pipe 102 that probe 100 is intended be used within.

As the transmission path of the electromagnetic radiation from transmitter 106 travels through the wall of pipe 102 twice, the response of probe 100 is not limited to the wall thickness of the incoming signal at detectors 108, but also includes effects of the wall thickness at transmitter 106. This creates anomalies that do not directly match the an actual defect. The response can be separated in to two responses, the effect seen when the defect length is greater than the distance between transmitter 106 and detectors 108 and the response for defects shorter than the distance between transmitter 106 and detectors 108.

Figure 5A:
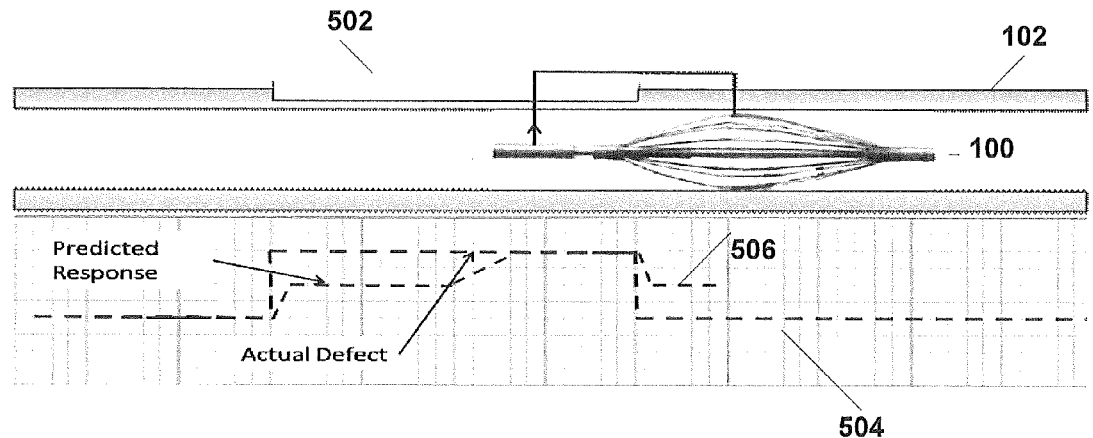
FIGS. 5A through 5F illustrate the predicted response of a probe to defects in a pipe according to some embodiments of the present invention.
Figure 5B:
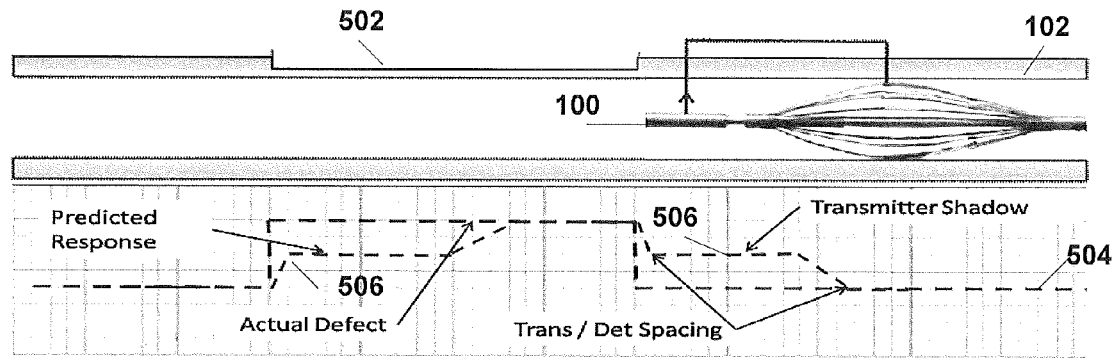

FIGS. 5A and 5B illustrates the response of probe 100 to a defect 502 in pipe 102 of length greater than the distance between transmitter 106 and detectors 108. In this case, the spacing between transmitter 106 and detectors 108 is greater than twice the diameter of pipe 102, resulting in detectors 108 measuring the remote-field signal.

FIG. 5A illustrates probe 100 at a position where transmitter 106 is adjacent to defect 502 while detectors 108 have traversed defect 102. As shown in the accompanying log, the actual defect trace 504 indicates a perfect response to defect 502. Predicted response 506 indicates the predicted response of detectors 108. The first response in detectors 108 is from the electromagnetic field re-entering the pipe. This signal comprises the summation of the thickness of the undisturbed wall and the thickness of the wall with defect 502. As show in trace 506, a response that is 50% of the actual defect is measured. The vertical resolution of the change will be approximately equal to the length of the sensor utilized in detector 108. In some embodiments, the length of detector 108 can be, for example, approximately 2 inches. In general, detectors 108 can have any length and can be of any type capable of detecting the fields.

When both detectors 108 and transmitter 106 are within defect 502, the response will reflect the actual thickness of the wall of pipe 102 at defect 502. As shown in trace 506, the transition from the 50% value of the actual defect trace 504 to the 100% value of the actual defect trace 504 will reflect the length of transmitter 106. In some embodiments, transmitter 106 can be between 4 and 6 inches in length. In general, transmitter 106 can be of any length and type capable of producing the fields.

As shown in FIG. 5B, when detectors 108 leave the trailing edge of defect 502, the predicted response as illustrated by trace 506 returns to the 50% value of the actual defect response trace 502 for the defect thickness. Again, the transition reflects the detector sensor length. Finally, transmitter 106 exits defect 502 and the response returns to the nominal thickness. Again, the transition response reflects the length of transmitter 106. As shown in FIG. 5B, the response of probe 100 will exceed the actual length of defect 502 by the distance equal to the spacing between transmitter 106 and detectors 108.

Figure 5C:
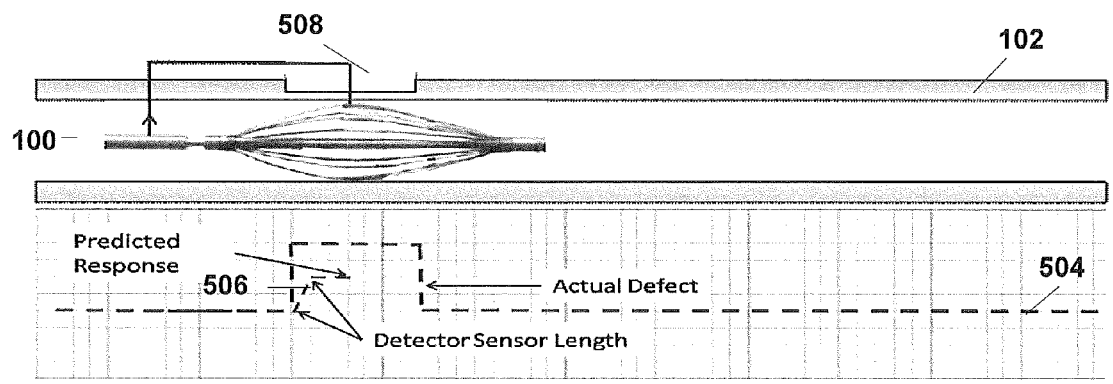

FIGS. 5C through 5F illustrate the response of probe 100 to defects 508 that have a length less than the spacing between transmitter 106 and detectors 108. In that case, a different effect is observed. As illustrated in FIG. 5C, similar to the example illustrated in FIGS. 5A and 5B, as probe 100 encounters defect 508, the first response is from the remote field re-entering pipe 102. The detected signal includes the summation of the thickness of the undisturbed wall and the thickness of the wall with defect 508. The result will be a response that is 50% of the actual wall thickness at defect 508, as is shown in predicted response trace 506 compared to the actual defect trace 504.

Figure 5D:
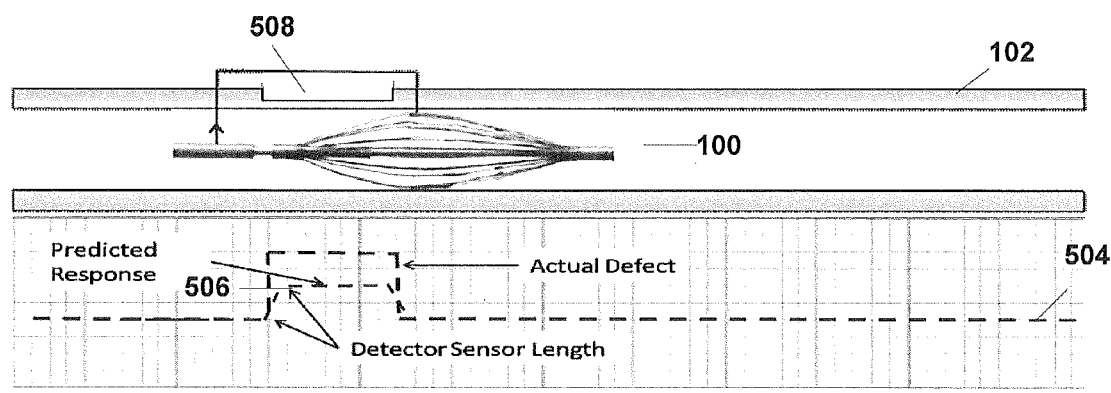
Figure 5E:
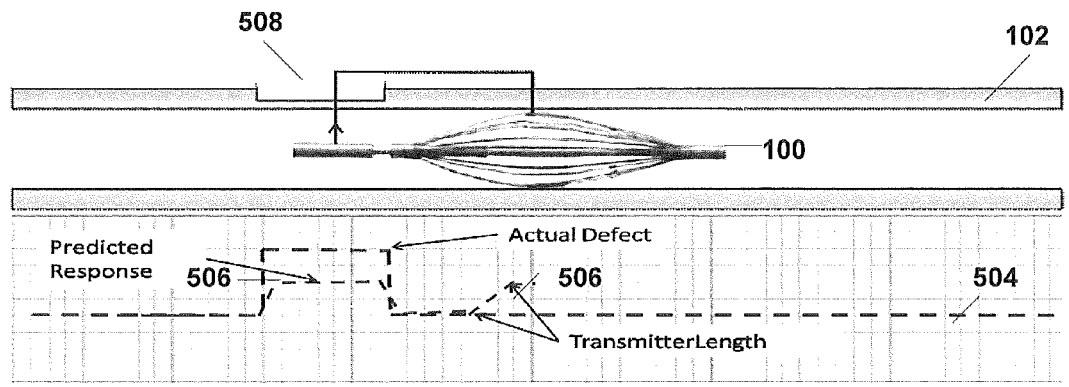

In this case, as is shown in FIGS. 5D and 5E, detectors 108 exit defect 508 before transmitter 106 enters defect 508. The results are a response of equal length to defect 508, but responding at 50% of the actual depth of the wall at defect 508 as illustrated in trace 504. As transmitter 106 enters defect 508, the transmission path now again includes effects of the same defect 508 with a value of 50% of the thickness of the wall at the actual defect 508 illustrated in trace 504.

Figure 5F:
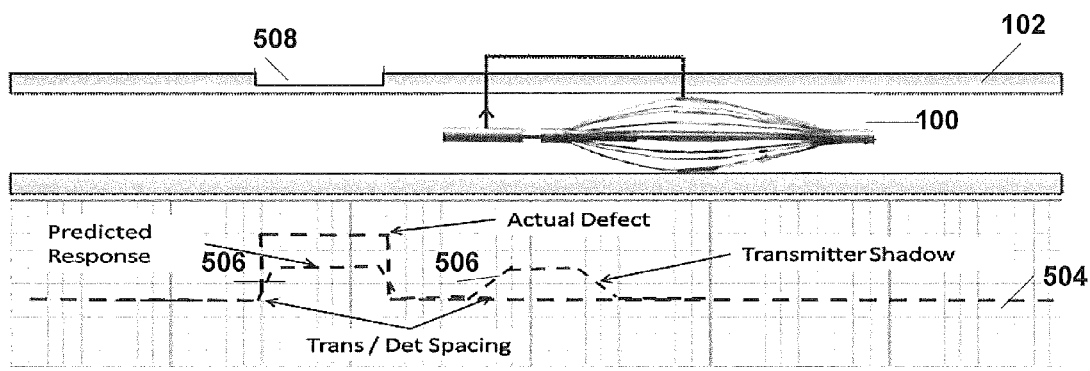

Finally, as illustrated in FIG. 5F, transmitter 106 exits defect 508, producing a duplicate and false effect at a distance from the actual defect equal to the spacing between transmitter 106 and detector 108. The shadow effect illustrated in trace 506 of FIGS. 5E and 5F is commonly viewed on the log just above each tubing/casing collar. Correction software allows for the removal of the shadow for easily recognizable anomalies, such as collars. However, correction for defect shadows from defects such as defect 508 are more difficult to identify and correct.

Figure 6:
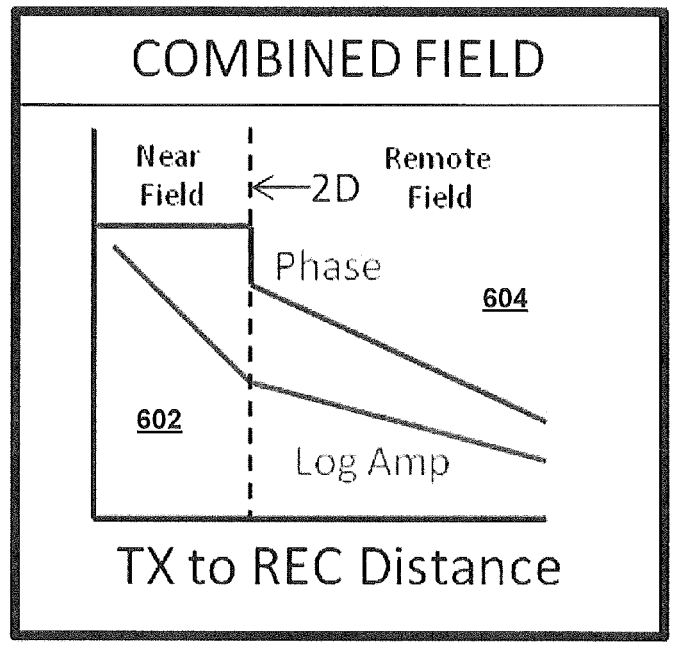
FIG. 6 illustrates the relationship between the phase and amplitude of the combined remote and near field received signal with increasing transmitter to detector spacing.

FIG. 6 illustrates the signal detected by detector 108 as a function of the separation distance between transmitter 106 and detector 108. As shown in FIG. 6, in near field region 602 the received signal at detector 108 is dominated by the near field signal shown in FIG. 4A. In the remote field region 604, the received signal at detector 108 is dominated by the remote field signal shown in FIG. 4B. The cross-over point (i.e., the point after which the amplitude of the remove field signal exceeds the amplitude of the near field signal) occurs at approximately twice the diameter of pipe 102.

Figure 7:
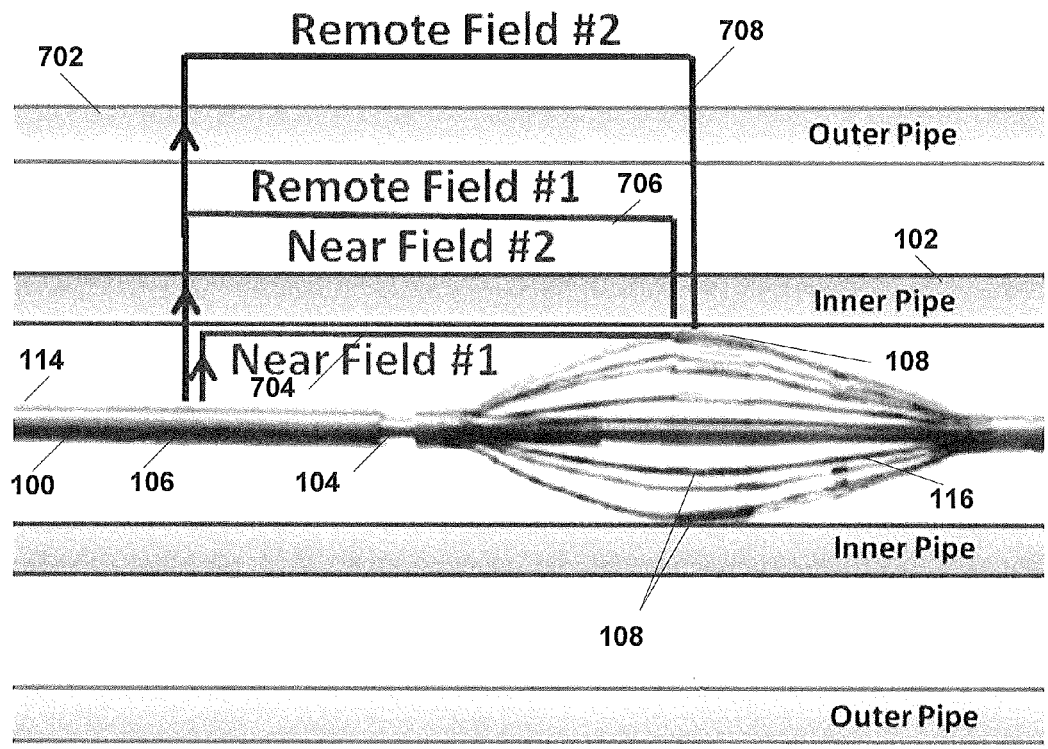
FIG. 7 illustrates a detector system in a two-pipe configuration according to some embodiments of the present invention in a multi-pipe configuration.

FIG. 7 illustrates an example where multiple concentric pipe strings are encountered in the well bore. In general there can be any number of concentric pipes. For purposes of illustration, two concentric pipes (pipe 102 positioned within pipe 702) are illustrated.

As is illustrated in FIG. 7, the remote field eddy current radiates on exiting the outer wall of innermost pipe 102. The inner pipe 102 now acts like a virtual RFEC logging tool, with its own relative Near Field signal and a corresponding Remote Field signal through the wall of outer pipe 702. As shown in FIG. 7, detectors 108 can receive three fields: Near Field 704, Field 706, and Field 708.

As described above, the spacing between transmitter 106 and detector 108 determines which of these fields (fields 704, 706, or 708) are recorded by detectors 108. If the spacing between transmitter 106 and detectors 108 is greater than two (2) times the diameter of outer pipe 702, then the recorded phase shift is substantially proportional to the thickness of both strings of pipe, pipe 702 and pipe 102. If, however, the spacing between transmitter 106 and detectors 108 is greater than two (2) times the diameter of inner pipe 102, but less than two (2) times the diameter of outer pipe 702, then the recorded signal is comprised of field 706, the Remote Field of inner pipe 102, that follows the path of the outer pipe's Near Field. The phase shift of this signal is, then, proportional to the thickness of inner pipe 102 only.

As described above, selection of the specific Remote Field signal can be achieved in multiple pipe environments through the careful design of the spacings between transmitter 106 and detectors 108. Application of this technique involves either running two passes with logging tools configured with different spacings between transmitter 106 and detectors 108 or by the use of multiple detectors 108 with appropriate spacings. For example, probe 100 may have first detectors 108 spaced greater than twice the diameter of pipe 102 from transmitter 106 and second detectors 108 spaced greater than twice the diameter of pipe 702 from transmitter 106.

Figure 8A:
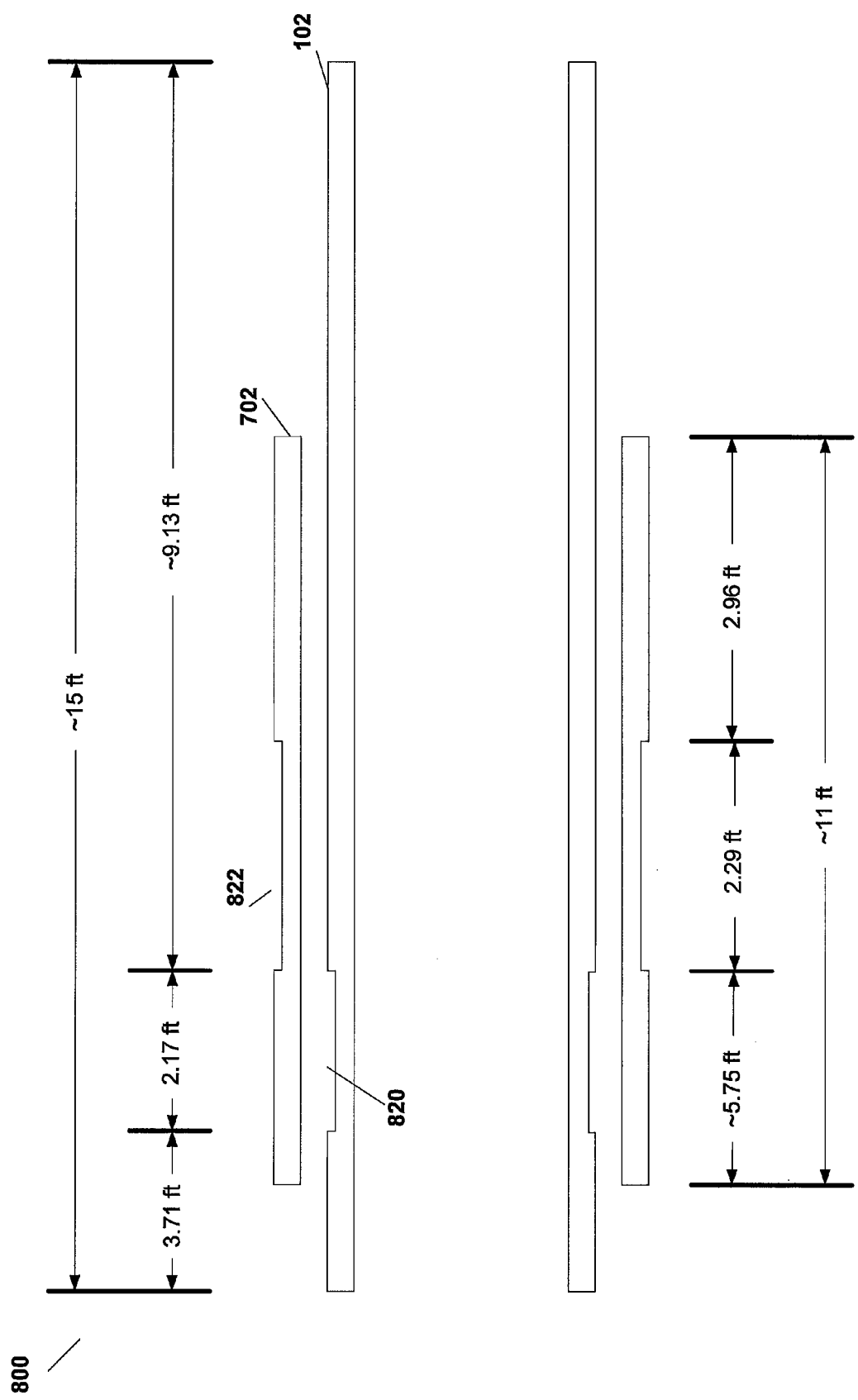
FIG. 8A illustrates a test jig utilized to demonstrate some embodiments of the present invention.
Figure 8B:
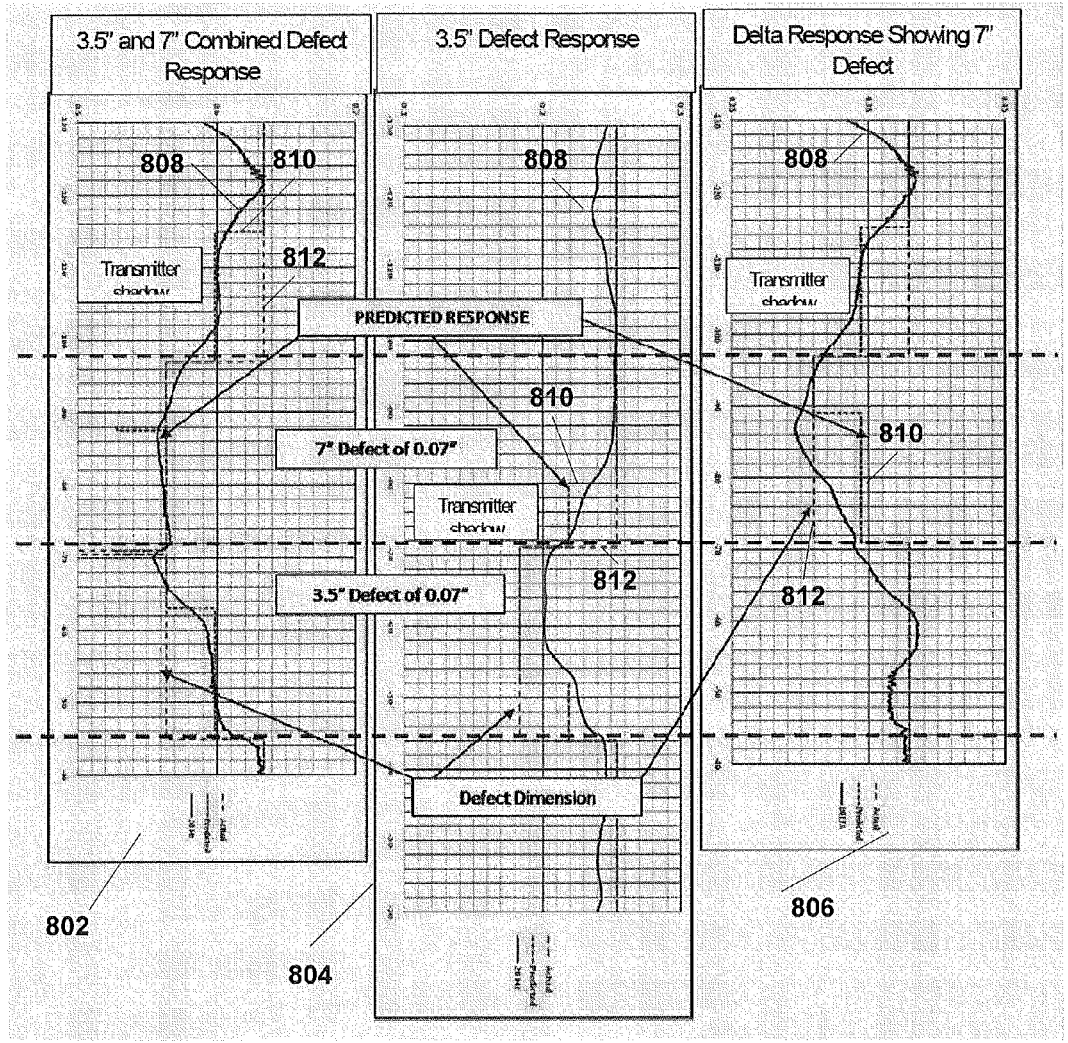
FIG. 8B illustrates the signal received in a multi-pipe system from the test jig illustrated in FIG. 8A.

FIG. 8B illustrates phase logs produced by an embodiment of probe 100 in a test jig 800, which is illustrated in FIG. 8A. Test jig 800, as shown in FIG. 8A, was constructed such that pipe 102 utilized a 3.5 inch outer diameter, 9.3 lb tubing approximately 15 ft (180 inches) long. Pipe 102 and is centered in pipe 702, which is a section of 7 inch, 26 lb casing approximately 11 ft long. An external defect in the form 820 of a thickness reduction of approximate 0.07 inch for 2.17 ft (26 inches) was milled approximately 3.71 ft (3 feet 8.5 inches) from one end of pipe 102. A similar defect 822 with a thickness reduction of approximately 0.07 inches for 2.29 ft (27.5 inches) was milled 2.96 ft (2 feet and 11.5 inches) from an end of casing pipe 702. Defects 820 and 822 are placed such that defect 820 in pipe 102 ended at the same point as the beginning of defect 822 in pipe 702 began.

Probe 100 was arranged such that the spacing between transmitter 106 and one of detectors 108 was approximately 8 inches to 10 inches (a reduction in spacing from a more typical 18 inch spacing). This spacing places this detector 108 at a spacing above the twice diameter Remote Field requirement for the 3.5 inch tubing of pipe 102 and within the Near Field region of field 706 of the 7" casing of pipe 702. Calibration for this detector 108 was performed assuming a response to only the 3.5" tubing of pipe 102. Further detectors 108, which in this example included 11 detectors were at the more typical 18 inch spacing to record the Remote Field response 708 from both of pipes 102 and 702. In the test described, one of the 12 detectors normally axially located at a 30° separation was relocated from a separation of 18 inches from transmitter 106 to a closer distance of 8 to 10 inches from transmitter 106. Calibration for the remaining detectors 108 was performed assuming the response was indicative of the sum of the thicknesses of both pipes 102 and 702. Some embodiments of the present invention can have any number of detectors with first detectors 108 located at a distance from transmitter 106 that is twice the diameter of inner pipe 102 but less than twice the diameter of outer pipe 702 and second detectors 108 located at a distance from transmitter 106 that is at least twice the diameter of outer pipe 702.

Two separate logs were produced from this test using test jig 800 described above and the example probe 100 described above. Log 802 is determined from detectors 108 positioned at the 18 inch spacing from transmitter 106. Log 804 is determined from the detectors 108 with the 8-10 inch spacing from transmitter 106. Log 806 was produced by subtracting log 804 from log 802, in other words by subtracting the signal that is responsive to pipe 102 from the combined results of pipe 102 and pipe 702.

Logs 802 and 804 show the thickness of the pipe measured from the phase shift response of the detected signal with respect to the transmitted signal measured by detectors 108 as a function of the depth within pipe 102. Logs 802 and 804 range from −130 to −40 inches. Log 802 illustrates the signal 808 from a 20 Hz transmitter 106, a predicted result 810, and the actual result 812.

In some embodiments, the phase shift can be converted to thickness. The skin depth (δ) is defined as the depth in any material at which the amplitude of a signal has been attenuated to 1/e, or 37%, of the original transmitted amplitude and the depth at which the phase lag is equal to 1 radian (~57.3°). At a depth of two Skin Depths, the amplitude has attenuated to $1/e^2$ or 14% of the original transmitted amplitude and 5% at 3 Skin Depths. Skin Depth in inches is given by the following equation:

$$\delta = \frac{26}{\sqrt{\pi f \mu_r \sigma_{\%}}}, \quad (1)$$

where δ is the skin depth in inches, f is the frequency in hertz, $\mu_r$ is the relative permeability (=$\mu/\mu_0$ to where $\mu_0$ to is the magnetic constant $4\pi \times 10^{-7}$ or $1.26 \times 10^{-6}$ henrey/meter and μ is the permeability of the pipe material), and $\delta_{\%}$ is the electrical conductivity expressed in the International Annealed Copper Standard (% IACS) given by $100*s/5.8 \times 10^7$ (Siemens/m) where s is the conductivity of the material given in Siemens/meter.

As Skin Depth (δ) also relates to phase lag θ where 1δ corresponding to a phase lag θ of one radian, the equation for phase relationship to thickness is given by:

$$\theta = \frac{d}{\delta} = \frac{d\sqrt{\pi f \mu_r \sigma_\%}}{26}, \quad (2)$$

where θ is the phase lag in radians and d is the thickness in inches.

In some embodiments, a partial saturation method can be utilized for the identification of magnetic permeability anomalies. In some embodiments, the calibration and processing method assumes that the relative magnetic permeability ($\mu_r$) and the electrical conductivity ($\delta_\%$) remain constant over the logged interval. In reality, magnetic permeability often changes over short intervals due to previous well intervention activities (wire line, CCL magnets, and coil-tubing operations) and from stress changes in the pipe. These magnetic anomalies can create false thickness changes that can be difficult to identify and are often mistaken to be pipe defects. However, the relative permeability may be altered by magnetizing the metal. At full magnetic saturation, the relative magnetic permeability variable is equal to unity. Full saturation eliminates the variability of the relative permeability and can allow for a better quantitative thickness determination.

A full saturation technique is commonly used for small sample sizes, but full saturation is difficult to achieve with a large metal mass, as the required magnetic field strength is difficult to attain. Although often failing to provide quantitative result, a partial saturation technique can be employed to identify permeability induced false responses and allow for a qualitative analysis. Partial saturation can be achieved with small but powerful rare earth magnets. This technique includes overlaying a base pass log with a post-magnetized log.

Figure 9:
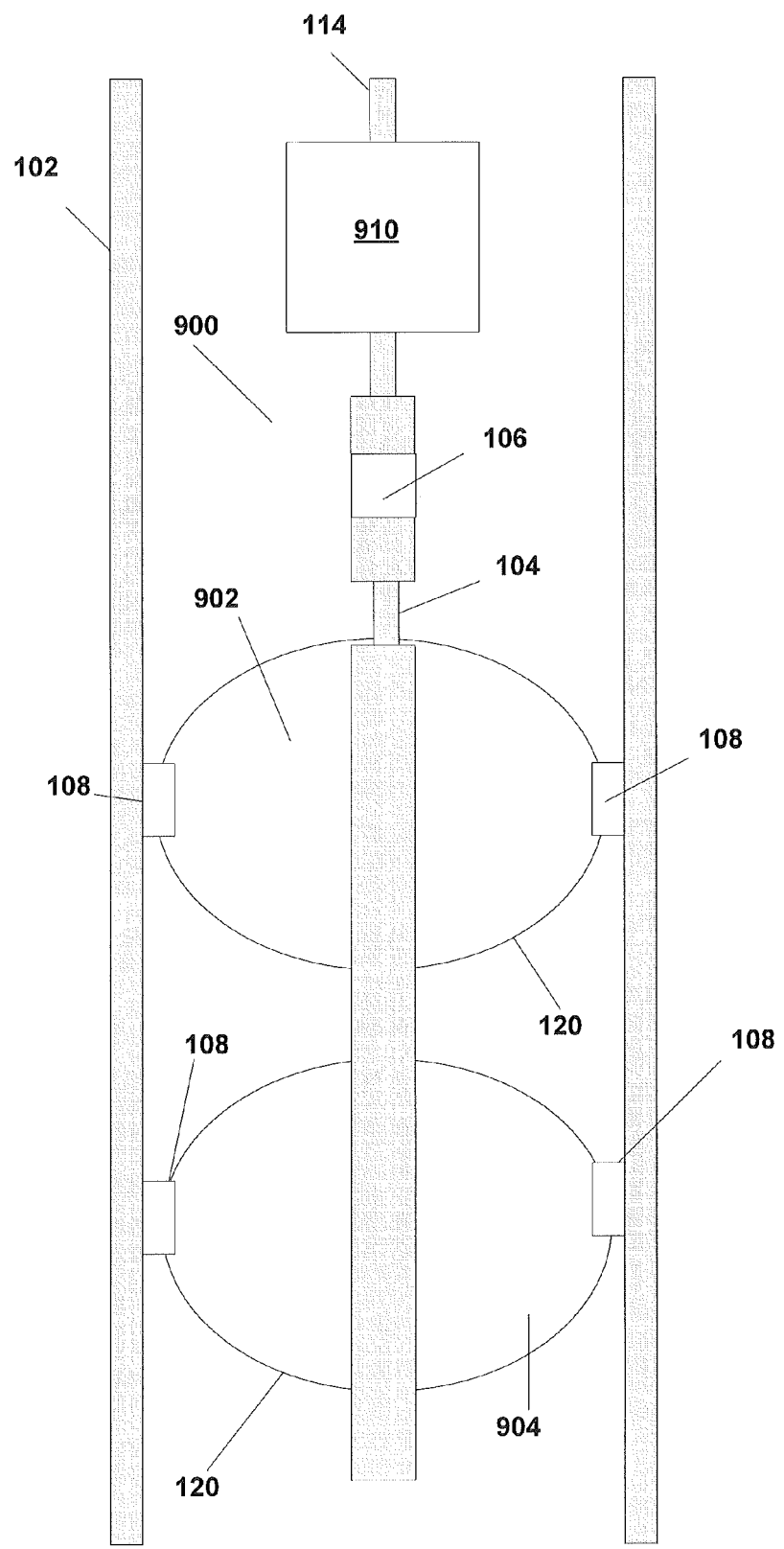
FIG. 9 illustrates a probe that can be utilized in a partial saturation technique.

These results can be achieved in some embodiments by addition of a magnetic sub to the top of the probe. FIG. 9 illustrates a probe 900 that can be utilized in a partial saturation pass. As shown in FIG. 9, a magnetic field generator 910 is provided. Magnetic field generator 910 can, for example, be a permanent magnet or can be a magnetic coil that is driven to provide the magnetic field. Magnetic field generator 910 is positioned such that, as probe 900 is inserted into pipe 102 (e.g., dropped into pipe 102), transmitter 106 and detectors 108 operate with sections of pipe 102 that have not yet been subjected to the magnetic field of magnetic field generator 910. As probe 900 is removed from pipe 102, the transmitter 106 and detectors 108 operate with sections of pipe 102 that have been previously exposed to the magnetic field of magnetic field generator 910.

As further illustrated with probe 900, first detectors 902 include detectors 108 that have a spacing from transmitter 106 that is less than those of second detectors 904. First detectors 902 can be spaced from transmitter 106 a distance greater than twice the diameter of pipe 102 but less than twice the diameter of a pipe 702 through which pipe 102 is inserted. Second detectors 904 can be spaced from transmitter 106 a distance greater than twice the diameter of pipe 702.

Figure 10:
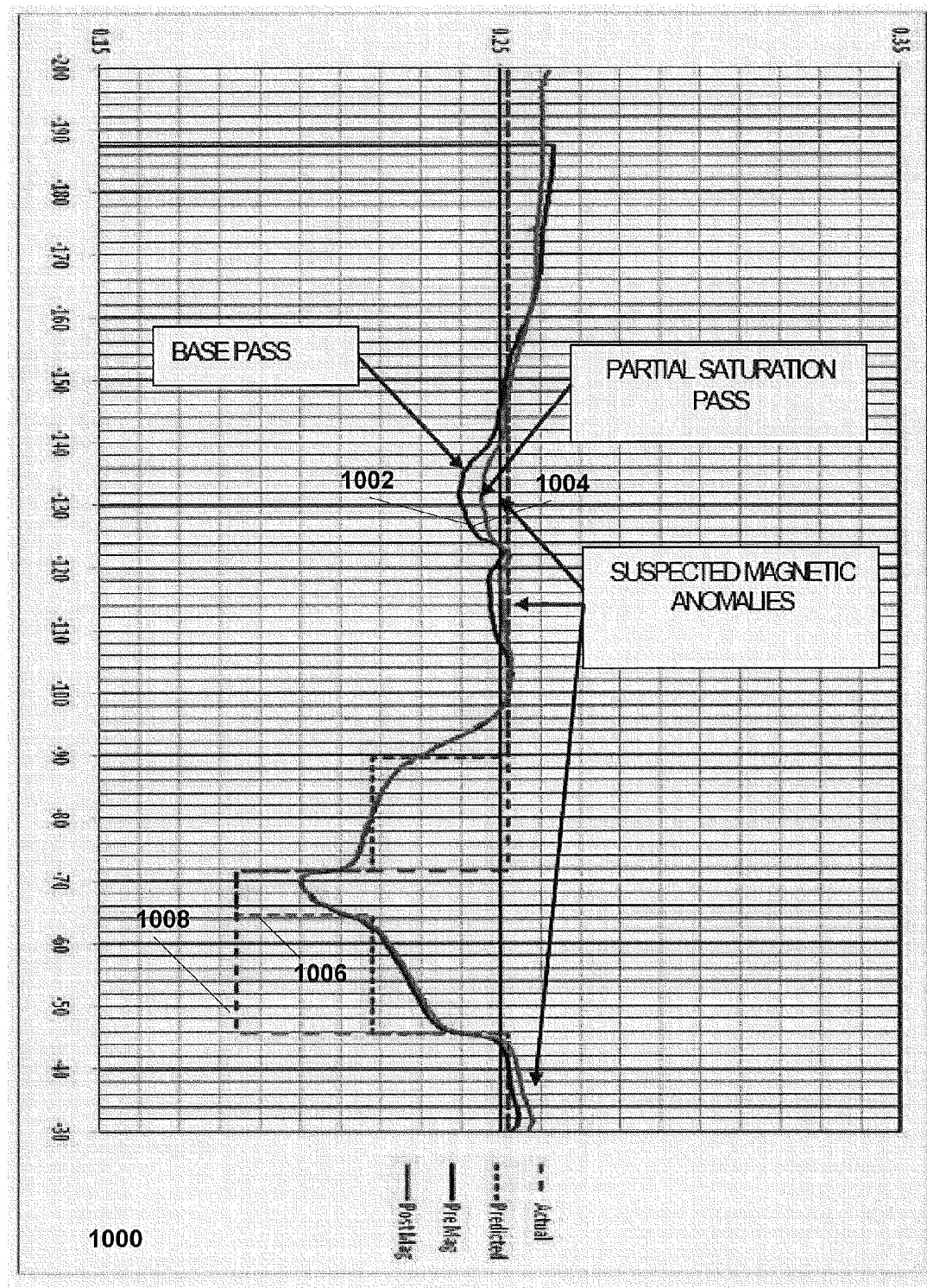
FIG. 10 illustrates a log from a technique where a base down log is recorded, followed by a partial saturation pass on the up log.

A base log can then recorded as probe 900 is inserted into pipe 102, followed by recording of a partial saturation log as probe 900 is removed from pipe 102. An example of this technique in the test jig is shown in FIG. 10. FIG. 10 shows a log 1000 with a base line 1002, a partial saturation pass 1004, a predicted response 1006, and an actual response 1008. As shown in FIG. 10, magnetic anomalies can be identified where there are deviations between the base line 1002 and the partial saturation pass 1004.

The partial saturation technique may be difficult to achieve in multiple pipe configurations with magnetic permeability changes in the external pipe. In that case, a magnetic field that saturates both pipe 102 and pipe 702 can be difficult to achieve. It should, however, allow for identification of permeability affects created by the inner string pipe 102.

Figure 11:
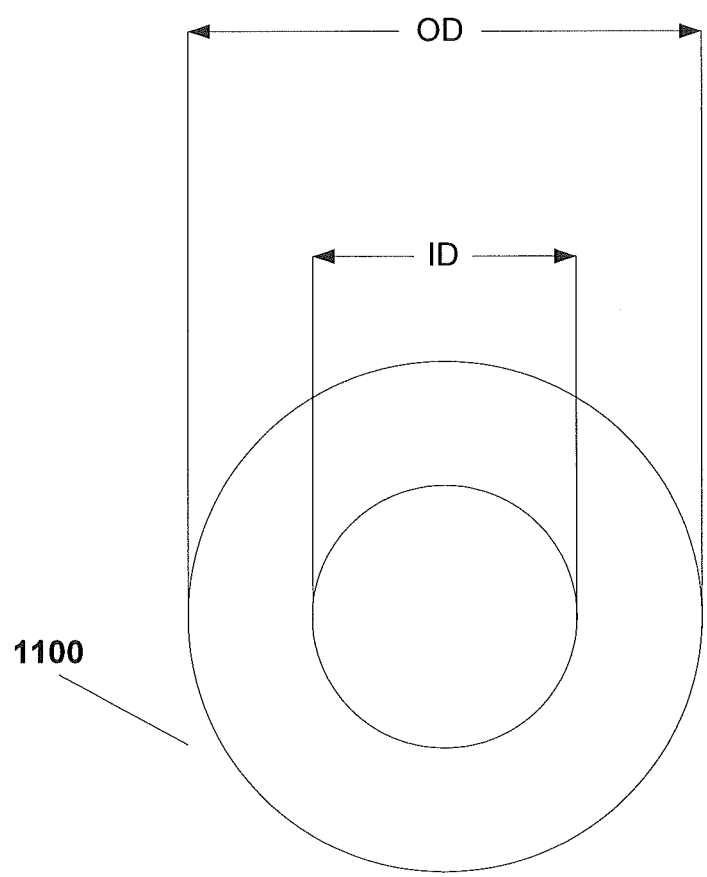
FIG. 11 illustrates a pipe utilized in modeling techniques according to the present invention.

FIG. 11 illustrates a cross section of a single casing 1100 that can be utilized in modeling and demonstrating some embodiments of the present invention. As shown in FIG. 11, casing 1100 includes an inner diameter ID and an output diameter OD. In testing casing 1100, probe 100 or probe 900 are placed in the center of casing such that the moment of transmitter coil 106 is aligned with the longitudinal direction of the casing (i.e., along the length of casing 1100). For the purposes of this modeling, the ID of casing 1100 is 6 inches and the OD of casing 1100 can be 6.5, 7.0, 7.5, 8, 8.5, and 9.0 inches.

Figure 12:
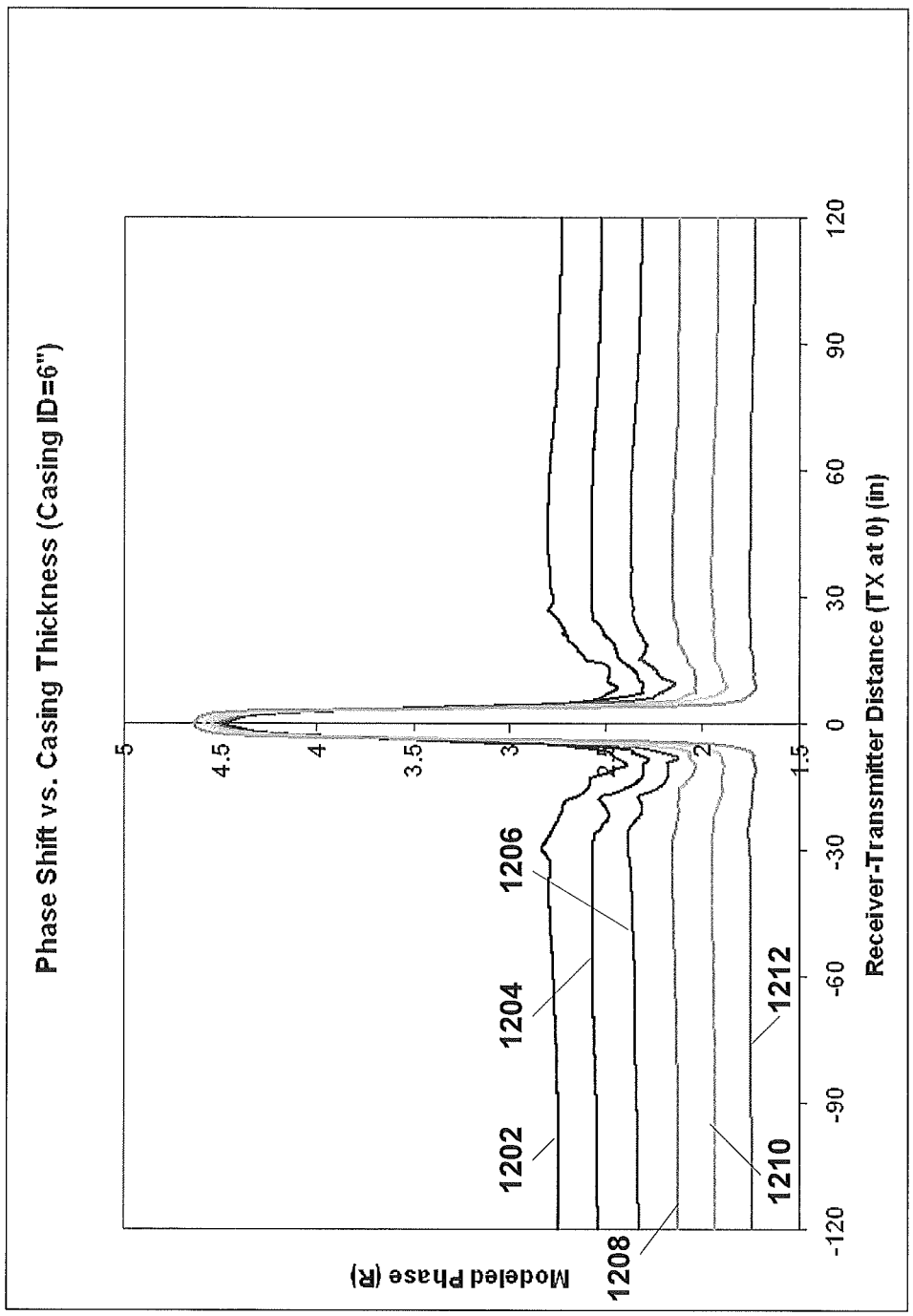
FIG. 12 illustrates the signal phase distribution versus casing thickness for the modeling illustrated in FIG. 11.

The signal phase distribution as a function of the separation between transmitter 106 and detector 108 for probe 100 operating on casing 1100 is shown in FIG. 12. As shown in FIG. 12, curve 1202 illustrates the phase θ for casing 1100 with ID=6 inches and OD=9 inches (wall thickness of 3 inches). Curve 1204 illustrates the phase θ for casing 1100 with ID=6 inches and OD=8.5 inches (wall thickness of 2.5 inches). Curve 1206 illustrates the phase θ for casing 1100 with ID=6 inches and OD=8.0 inches (wall thickness of 2.0 inches). Curve 1208 illustrates the phase θ for casing 1100 with ID=6 inches and OD=7.5 inches (wall thickness of 1.5 inches). Curve 1210 illustrates the phase θ for casing 1100 with ID=6 inches and OD=7.0 inches (wall thickness of 1.0 inches). Curve 1212 illustrates the phase θ for casing 1100 with ID=6 inches and OD=6.5 inches (wall thickness of 0.5 inches). As illustrated in FIG. 12, and discussed above, the signal phase θ increases proportionally with the casing thickness for separations far removed from 0 inches. The phase θ does not change much with a separation of approximately 0.

Figure 13:
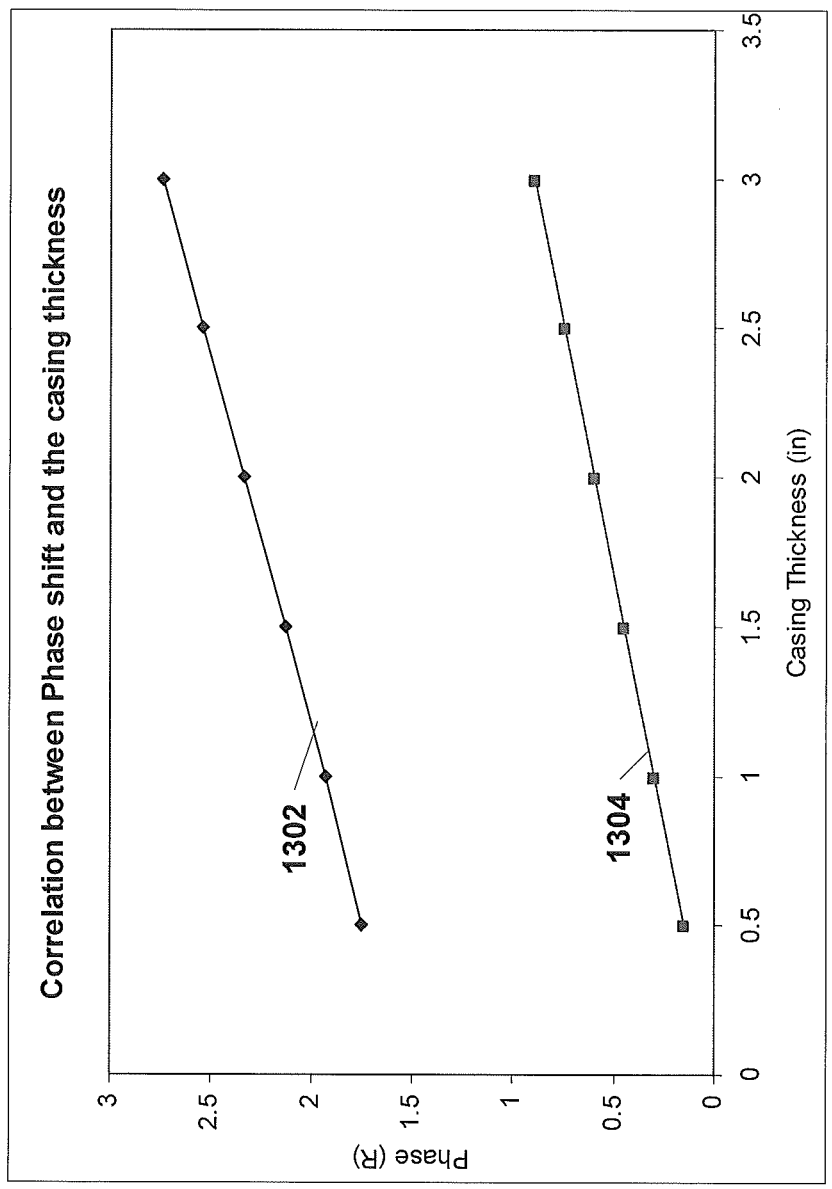
FIG. 13 illustrates the modeled phase-thickness correlation.

FIG. 13 illustrates a modeled phase shift curve 1302 and a phase shift curve 1303 generated from EQ. 2 for casing 1100 in the regime where the separation between transmitter 106 and detector 108 is large enough that the phase shift with changing separation remains unchanged. FIG. 13 illustrates that there is a proportional relationship between the casing thickness and the signal phase shift. Therefore, the casing thickness can be determined by the measured signal phases.

Figure 14:
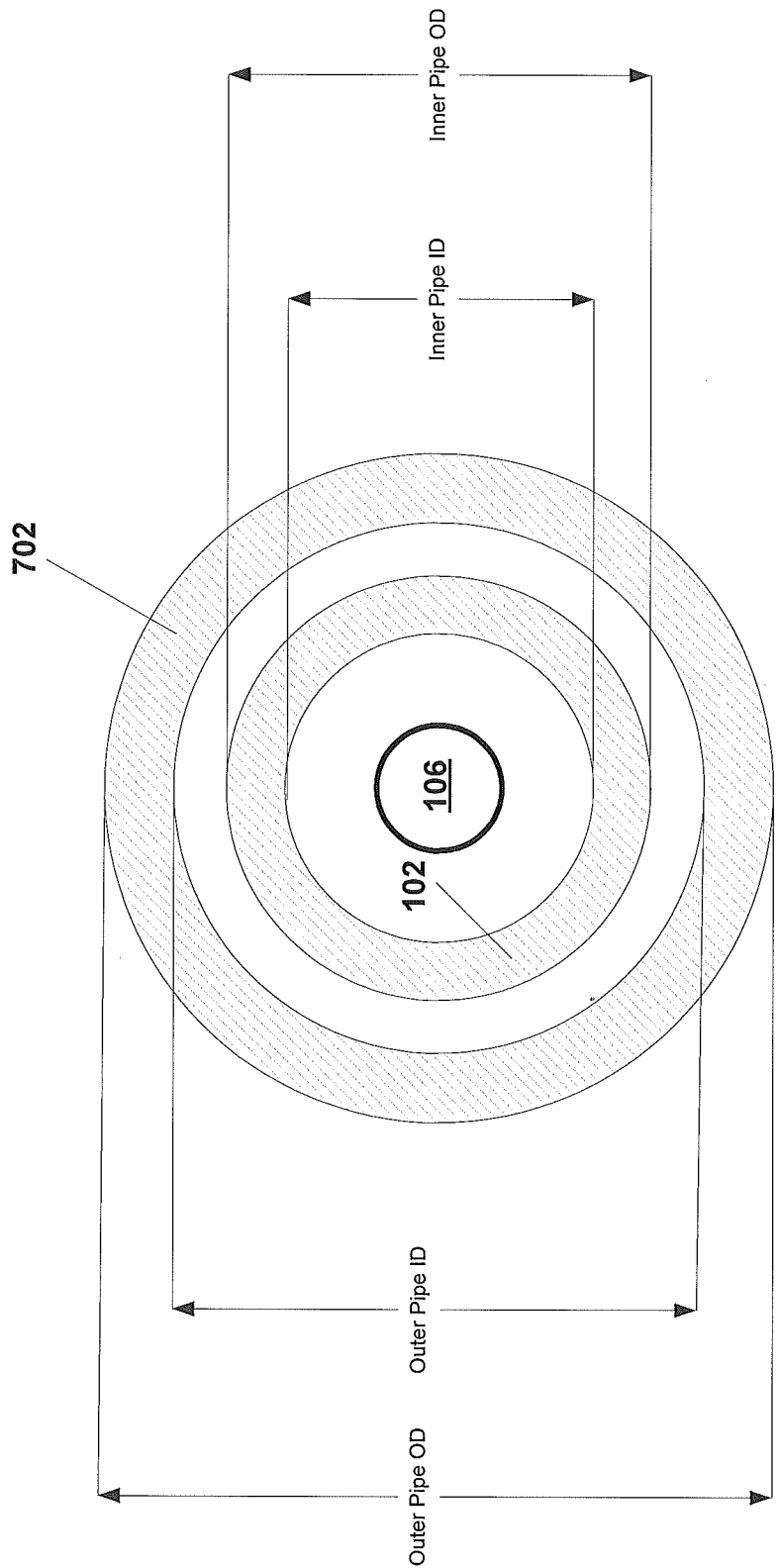
FIG. 14 illustrates a double casing model.

FIG. 14 illustrates a double casing model with an inner pipe 102 and an outer pipe 702, as shown in FIG. 7. For the purposes of this discussion, the ID of pipe 102 is taken as 3.5 inches and the ID of pipe 702 is taken as 6 inches. The thicknesses of pipes 102 and 702 are adjusted in the modeling when taking the signals at detectors 108 inside the inner casing (see FIG. 7). The thickness of pipe 102, designated $T_I$, is the difference between the inner pipe OD and the inner pipe ID. Similarly, the thickness of pipe 702, designated $T_O$, is the difference between the outer pipe OD and the outer pipe ID.

Figure 15:
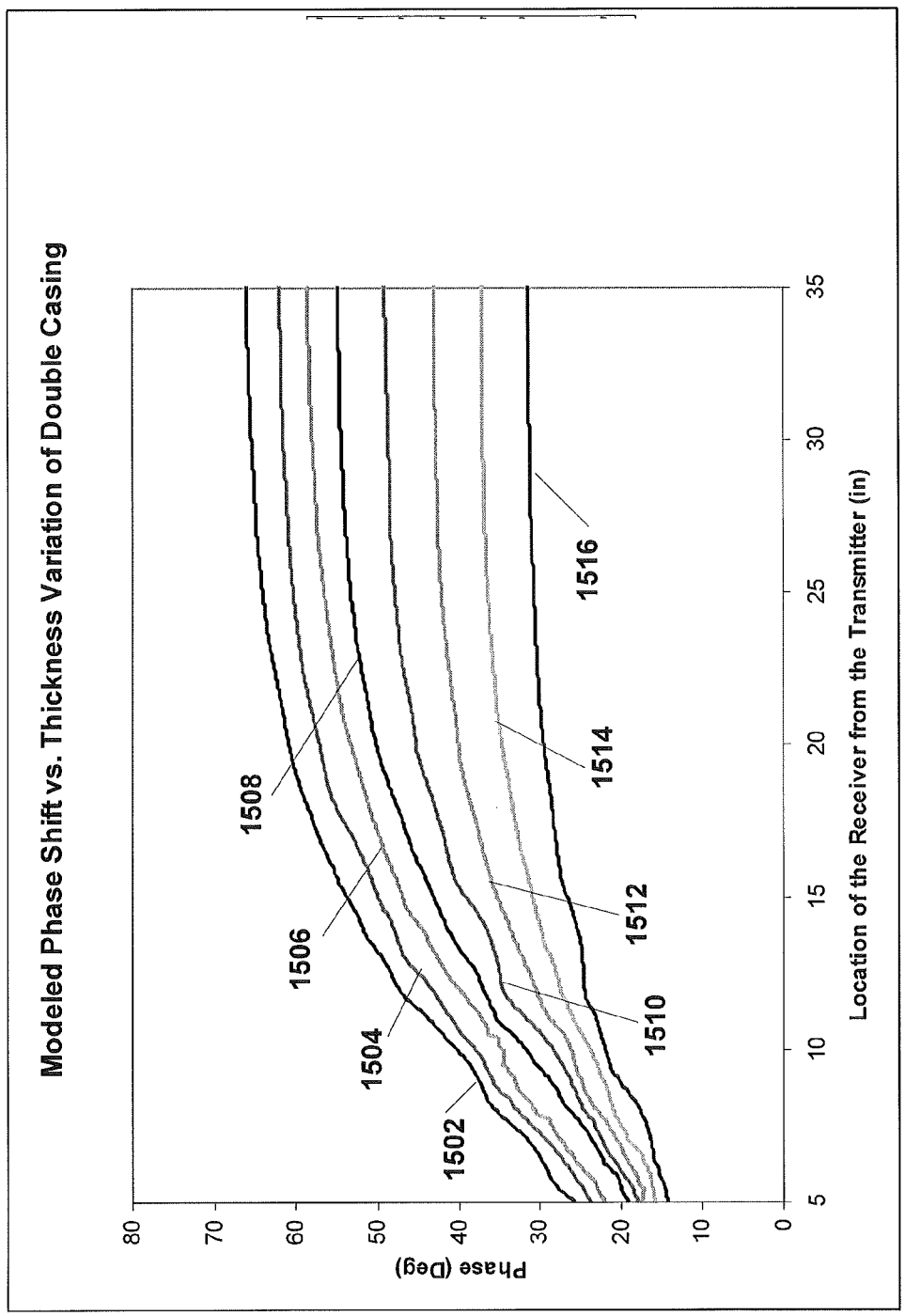
FIG. 15 illustrates a modeled signal phase verses thickness for both casings.

FIG. 15 shows the modeled phase shifts as a function of the separation between transmitter 106 and detector 108 for different combinations of thicknesses of pipe 102 and pipe 702. Trace 1502 corresponds to TO=2.00 inches and TI=2.00 inches. Trace 1504 corresponds to TO=2.00 inches and TI=1.75 inches. Trace 1506 corresponds to TO=2.00 inches and TI=1.50 inches. Trace 1508 corresponds to TO=2.00 inches and TI=1.25 inches. Trace 1510 corresponds to TO=1.75 inches and TI=1.25 inches. Trace 1512 corresponds to TO=1.50 inches and TI=1.25 inches. Trace 1514 corresponds to TO=1.25 inches and TI=1.25 inches. Trace 1516 corresponds to TO=1.00 inches and TI=1.25 inches.

FIG. 15 demonstrates that the overall phase is increasing with the total thickness of both casings 102 and 702 where detector 108 is well separated from transmitter 106. However, the sensitivity to the different casing is changing with different receiver separations. To illustrate the sensitivity phenomenon, two numerical experiments are carried: 1) Fix the thickness of the outer casing at 2.0 inches, change the thickness of the inner casing by a quarter inch; 2) Fix the inner casing at 2 inches, and change the outer casing thickness by a quarter inch. The modeled phase shifts are shown in FIG. 16.

Figure 16:
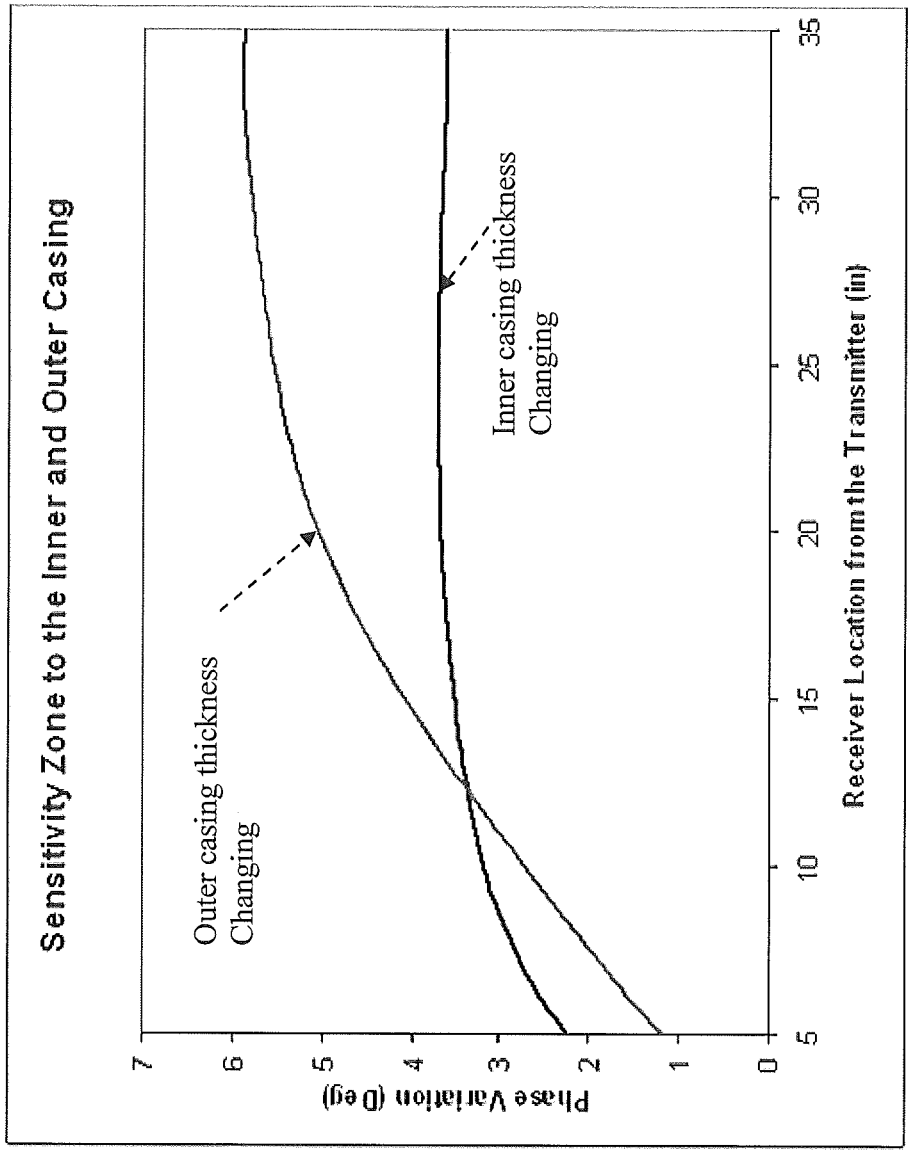
FIG. 16 illustrates modeled phase shifts from different casings.

FIG. 16 illustrates that the inner casing causes larger phase shift when the receiver is close to the transmitter, for example 5 inches. While the outer casing causes larger phase shift when detector 108 is farther from transmitter 106, for example farther than 15 inches. This phenomenon provides us a way to determine thickness of both casings.

Figure 17:
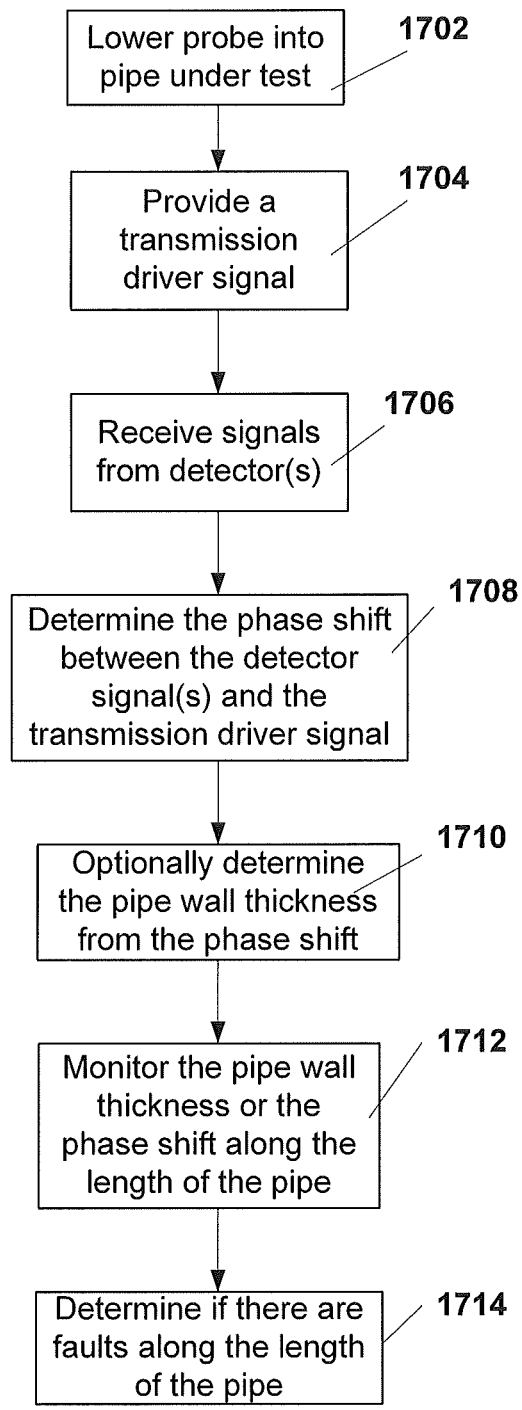
FIG. 17 illustrates a method of testing a pipe according to some embodiments of the present invention.

FIG. 17 illustrates a method of testing a pipe according to some embodiments of the present invention. In step 1702, probe 100 is lowered into pipe 102, the pipe-under-test. In step 1704, controller 128 directs transmitter driver 122 to provide a driving signal to transmitter 106 and to provide the driving signal to controller 128. The driving signal is a low frequency signal, for example between about 5 Hz and about 20 Hz.

In step 1706, detection circuit 124 receives the signals from one or more detectors 108 and provides the detector signals to controller 128. In some embodiments, signals provided to controller 128 can be digital signal. In some embodiments, controller 128 may include analog circuitry to compare the driving signal with the detector signals. In step 1708, controller 128 determines the phase shift between the detector signal received by detection circuit 124 and the driving signal generated by transmitter driver 122. If probe 100 includes multiple detectors 108, detectors 108 may be placed at separations from transmitter 106 that allow for the detection of thicknesses through multiple pipes (as is illustrated in FIG. 7). In step 1710, the wall thickness can be determined from the phase shift. In some embodiments, step 1710 is omitted and the wall thickness is never calculated in the testing process. In some embodiments, the wall thickness can be determined by controller 128. In some embodiments, the wall thickness can be determined by computer 134. Computer 134 can then generate a log of wall thickness or phase shift as a function of the position of probe 100 in pipe 102. In some embodiments, in step 1714 computer 134 can detect faults along pipe 102 based on the wall thickness measurements. In some embodiments, step 1714 is performed by a user inspecting a log of wall thickness or phase shifts generated by computer 134.

Figure 18:
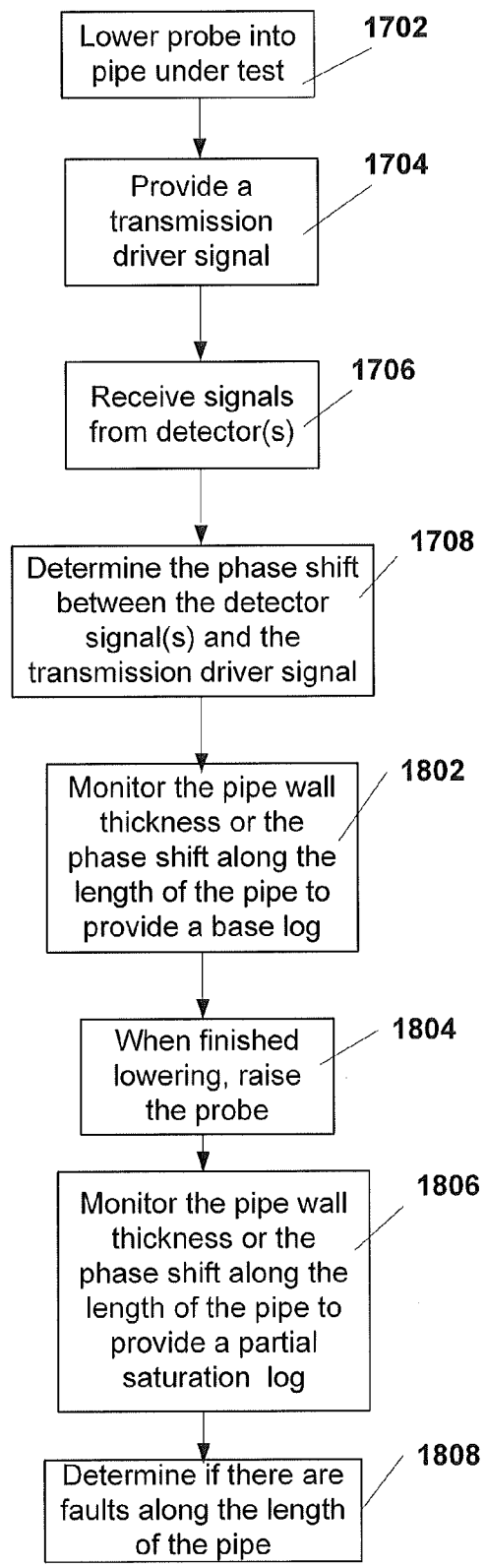
FIG. 18 illustrates a method utilizing a partial saturation technique for testing a pipe according to some embodiments of the present invention.

FIG. 18 illustrates a method for performing a partial saturation test on pipe 102 utilizing probe 900 as shown in FIG. 9. As in FIG. 17, probe 900 controller 128 directs cable controller 126 to lower probe into pipe 102 in step 1702. In step 1704, controller 128 directs transmitter driver 122 to provide the driving signal to transmitter 106. In step 1706, detection circuit 124 receives signals from detectors 108 and provides detector signals to controller 128. In step 1708, controller 128 determines the phase shift between the driver signal from transmitter driver 122 and the detector signal from detection circuit 124. In step 1802, the phase shift or wall thickness is monitored as probe 900 is lowered into pipe 102 to provide a base log. In step 1804, when probe 900 is as far into pipe 102 as is desired for the particular test, which may be somewhat short of the entire length of pipe 102, the controller 128 directs cable controller 126 to raise probe 900. In step 1806, the phase shift or wall thickness is monitored as probe 900 is raised in pipe 102 to provide a partial saturation log. In step 1808, the base log and the saturation log are compared for magnetic anomalies and the a determination is made whether or not there are defects or faults along the length of pipe 102. In some embodiments, step 1802, 1806, and 1808 are performed by computer 134, although parts of those functions may be performed by controller 128.

The above detailed description is provided to illustrate specific embodiments of the present invention and is not intended to be limiting. Numerous variations and modifications within the scope of the present invention are possible. The present invention is set forth in the following claims.

What is claimed is:

1. A method of inspecting a pipe, comprising:
    lowering a probe into a first pipe, the first pipe being concentrically placed within a second pipe, the probe including a transmitter, a first detector separated from the transmitter by a first distance equal to or greater than twice a diameter of the first pipe, and a second detector separated from the transmitter by a second distance equal to or greater than a diameter of the second pipe;
    providing a driving signal to the transmitter;
    receiving a first detector signal from the first detector;
    receiving a second detector signal from the second detector;
    determining a first phase shift between the first detector signal and the driving signal;
    determining a second phase shift between the second detector signal and the driving signal;
    determining a wall thickness of the first pipe from the first phase shift;
    determining a total wall thickness from the second phase shift; and
    subtracting the wall thickness of the first pipe from the total wall thickness to determine a wall thickness of the second pipe.

2. The method of claim 1, further including monitoring one of the first phase shift and the second phase shift as a function of location in the pipe.

3. The method of claim 1, further comprising:
    modeling a response of the probe to known defect; and
    determining a fault in one of the first pipe and the second pipe based on one of the first phase shift and the second phase shift.

4. The method of claim 3, wherein modeling a response includes providing a predicted response based on a length of the defect and dimensions of the probe.

5. The method of claim 1, wherein the probe further includes a magnetic field generator and the method further includes
    generating a base log from the phase shift as a function of location in the pipe as the probe is lowered into the pipe; and
    generating a partial saturation log from the phase shift as a function of location in the pipe as the probe is raised in the pipe.

6. A method of determining thickness of a pipes in a multi-pipe configuration, comprising:
    lowering a probe into the multi-pipe configuration, the probe including
        a transmitter,
        at least one first detector spaced from the transmitter by a distance greater than a first diameter of a first pipe of the multi-pipe configuration and less than a second diameter of a second pipe of the multi-pipe configuration, and
        at least one second detector spaced from the transmitter by a distance greater than the second diameter;
    measuring a first phase shift from the at least one first detector;

measuring a second phase shift from the at least one second detector;

determining a first wall thickness of the first pipe from the first phase shift;

determining a combined wall thickness from the second phase shift; and determining a second wall thickness from the difference between the combined wall thickness and the first wall thickness.

7. A system for testing a first and second pipes, the first pipe being concentrically disposed within the second pipe, the system comprising:

a probe including a transmitter, a first detector separated from the transmitter by a first distance at least twice that of the inner diameter of the first pipe, a second detector separated from the transmitter by a second distance at least twice that of the inner diameter of the second pipe; and a processor coupled to the transmitter and the first and second detectors and operable to determine first and second phase shifts of signals received at the first and second detectors, respectively, relative to a signal transmitted by the transmitter and to determine a wall thickness of the first pipe from the first phase shift, a combined wall thickness from the second phase shift, and a wall thickness of the second pipe from a difference between the combined wall thickness and the first wall thickness.

8. The system of claim 7, further comprising:
a transmitter driver coupled to the transmitter; and
a detection circuit coupled to one of the first and second detectors.

9. The system of claim 8, further including an interface to a computer, the computer operable for determining a fault based on the first and second phase shifts and a model of a predicted response of the probe to a known defect.

10. The system of claim 7 further comprising a cable controller coupled to the processor, the cable controller operable for controlling the position of the probe in the first pipe.

11. The system of claim 7 wherein the probe further includes a magnetic field generator separated from the transmitter and the first and second detectors.

12. The system of claim 11, wherein the magnetic field generator includes a permanent magnet.

13. The system of claim 11, wherein the magnetic field generator includes a coil driving by a current.

* * * * *